(12) United States Patent
Kuroda et al.

(10) Patent No.: US 9,080,974 B2
(45) Date of Patent: Jul. 14, 2015

(54) OBSERVATION DEVICE AND METHOD OF OBSERVING

(75) Inventors: Hiroto Kuroda, Tama (JP); Shin Yoneya, Maebashi (JP); Motoyoshi Baba, Nakano-ku (JP); Masayuki Takasu, Abiko (JP)

(73) Assignee: SEVENTH DIMENSION DESIGN, INC., Chuo-Ku, Kobe Hyogo (JP)

( * ) Notice: Subject to any disclaimer, the term of this patent is extended or adjusted under 35 U.S.C. 154(b) by 313 days.

(21) Appl. No.: 13/639,786

(22) PCT Filed: Apr. 4, 2011

(86) PCT No.: PCT/JP2011/058510
§ 371 (c)(1),
(2), (4) Date: Dec. 19, 2012

(87) PCT Pub. No.: WO2011/125972
PCT Pub. Date: Oct. 13, 2011

(65) Prior Publication Data
US 2013/0087724 A1    Apr. 11, 2013

(30) Foreign Application Priority Data

Apr. 6, 2010   (JP) .................................. 2010-087567
Oct. 14, 2010  (JP) .................................. 2010-231308
Jan. 7, 2011   (JP) .................................. 2011-001898

(51) Int. Cl.
*G01B 9/02*     (2006.01)
*G01N 21/59*    (2006.01)
*G01N 21/47*    (2006.01)

(52) U.S. Cl.
CPC ............ *G01N 21/59* (2013.01); *G01B 9/02024* (2013.01); *G01B 9/02091* (2013.01); *G01N 21/4795* (2013.01)

(58) Field of Classification Search
CPC .............. G01B 9/02; G01J 11/00; G01J 9/02; G01J 9/0246; G01N 21/45
USPC ........................................................ 356/450
See application file for complete search history.

(56) References Cited

U.S. PATENT DOCUMENTS

2005/0174578 A1* 8/2005 Wei .............................. 356/477
2005/0175540 A1* 8/2005 Oraevsky et al. .............. 424/9.5
(Continued)

FOREIGN PATENT DOCUMENTS

JP    11-244243 A    9/1999
JP    2000-037355 A  2/2000
(Continued)

OTHER PUBLICATIONS

Nouchi T., et al.,*Spectroscopic Measurement of Scattering Media by Parallel-Detection-Based Optical Coherence Tomography*, Optical Review, Dec. 1, 2005, vol. 12, No. 6, p. 486-489.
(Continued)

*Primary Examiner* — Tarifur Chowdhury
*Assistant Examiner* — Md Rahman
(74) *Attorney, Agent, or Firm* — Larry E. Henneman, Jr.; Gregory P. Gibson; Henneman & Associates, PLC

(57) ABSTRACT

Provided is an observation device and a method of observing capable of clearly obtaining information relating to a boundary part where a medium inside an observation object changes. An observation device (1) is a device for observing an observation object (2) including a sensitivity factor in which a dipole moment changes by sensing an electromagnetic wave (31). An output part (11) outputs the electromagnetic wave (31) and the dipole moment of the sensitivity factor included in the observation object (2) is changed by the electromagnetic wave (31). A detector part (12) detects, of the electromagnetic wave (31) outputted from the output part (11), a signal electromagnetic wave (33) which comes through the observation object (2) and a reference electromagnetic wave (32) which bypasses the observation object (2). A control part (13) analyzes the structure of the observation object (2) based on the detection results of the detection part (12). The electromagnetic wave (31) is pulse laser light which is intermittently outputted in pulse waveform. The wavelength of the electromagnetic wave (31) is arranged within the wavelength absorption band of the sensitivity factor.

16 Claims, 18 Drawing Sheets

(56) References Cited

U.S. PATENT DOCUMENTS

| | | | |
|---|---|---|---|
| 2006/0162771 A1* | 7/2006 | Inoue et al. | 136/263 |
| 2007/0025638 A1* | 2/2007 | Ozcan et al. | 382/280 |
| 2009/0021746 A1* | 1/2009 | Toida et al. | 356/484 |
| 2010/0110440 A1* | 5/2010 | Vaziri | 356/450 |

FOREIGN PATENT DOCUMENTS

| | | |
|---|---|---|
| JP | 2003-121347 A | 4/2003 |
| JP | 2004-340581 A | 12/2004 |
| JP | 2005-211355 A | 8/2005 |
| JP | 2007-260192 A | 10/2007 |
| JP | 2007-327935 A | 12/2007 |
| JP | 2008-272256 A | 11/2008 |
| JP | 2009-520548 A | 5/2009 |
| JP | 2009-128099 A | 6/2009 |

OTHER PUBLICATIONS

Povazay et al., *Submicrometer Axial Resolution Optical Coherence Tomography*, Optics Letters, Oct. 15, 2002, vol. 27, No. 20, p. 1800-1802.

JP Application No. 2011-001898, Office Action dated Feb. 25, 2011 (with English translation).

JP Application No. 2011-001898, Office Action dated Jun. 17, 2011 (with English translation).

International Application No. PCT/JP2011/058510, International Search Report dated Jun. 28, 2011 (with English translation).

International Application No. PCT/JP2011/058510, Written Opinion dated Jun. 28, 2011 (with English translation).

International Application No. PCT/JP2011/058510, International Preliminary Report on Patentability dated Nov. 13, 2012 (with English translation).

* cited by examiner

OBSERVATION DEVICE AND METHOD OF OBSERVING

TECHNICAL FIELD

The present invention relates to an observation device for observing an observation object and a method of observing.

BACKGROUND OF THE INVENTION

A variety of radar techniques have been proposed as a technique to obtain information about internal structure of an observation object by irradiating the object with an electromagnetic wave and receiving its reflected wave etc (for example, see Patent Document 1). This type of traditional radar device can, for instance, detect the electromagnetic wave reflected at a boundary part within the observation object where a medium changes, and obtain information about the structure inside the observation object (for example, objects etc present in the observation object) based on its detection result.

THE PRIOR ART DOCUMENT

[Patent Document 1] JP Tokukai 2007-327935

SUMMARY OF THE INVENTION

Problems to be Solved by the Invention

If variation of dielectric constants at boundary part of the medium in the observation object is small, however, the radar device in the traditional prior art 1 etc cannot substantially reflect an electromagnetic wave at the boundary part of the medium, thereby failing to detect the boundary part of the medium or obtaining only-unclear detection.

There are some instances that use contrast agents such as barium or pigment etc. in X-ray radiography of an observation object and so on. However, these contrast agents are intended to achieve sensitizing effect (such as improvement of contrast) of images to be taken, by creating shade inside the observation object while the observation object is irradiated with X-ray etc. This is essentially different in functions etc from induction factors of the present invention.

Therefore, the aim of the present invention is to provide an observation device and an observation method that can obtain enough information about boundary parts in the observation object where a medium changes.

Solution to Solve the Problems

In order to solve the problem above, in an aspect relating to an observation device of the present invention, an observation device for observing an observation object including an induction factor whose dipole moment changes by induction with the electromagnetic wave comprises an output part which outputs the electromagnetic wave and changes the dipole moment of said induction factor included in said observation object by the outputted electromagnetic wave; a detection part which detects a signal electromagnetic wave coming through said observation object and a reference electromagnetic Wave coming without passing through said observation object among electromagnetic waves outputted by said output part; and an analysis part which analyzes structures of said observation object based on detection result by said detection part, wherein said electromagnetic wave outputted by said output part is a pulsed laser light which is continuously outputted by in pulses, and wavelength of said electromagnetic wave outputted by said output part is set to be within an absorption wavelength region of the induction factor, which results in absorption of the irradiated electromagnetic wave by said induction factor.

Furthermore, in an aspect regarding an observation method of the present invention, a method of observing an observation object comprises a step of introducing into said observation object an induction factor whose dipole moment changes by induction with an electromagnetic wave; and a step of detecting a signal electromagnetic wave coming through said observation object and a reference electromagnetic wave coming without passing through said observation object among electromagnetic waves outputted by said output part, while the electromagnetic wave is outputted and the outputted wave changes the dipole moment of said induction factor included in said observation object, and of analyzing structure of said observation object based on detection result by said detection part, wherein said electromagnetic wave outputted by said output part is a pulsed laser light which is continuously outputted by in pulses, and wavelength of said electromagnetic wave outputted by said output part is set to be within an absorption wavelength region of the electromagnetic wave, which results in absorption of the irradiated electromagnetic wave by said induction factor.

Description of Terms

In the present invention, the term "a dipole moment of an induction factor changes" includes not only that size or orientation of the dipole moment of said induction factor changes, but also that the dipole moment is induced from the state of nothing.

Effects of the Invention

In the above-described aspect of the observation device of the present invention, an output part outputs an electromagnetic wave to an observation object, a detection part detects a signal electromagnetic wave coming through said observation object and a reference electromagnetic wave coming without passing through said observation object among electromagnetic waves outputted by said output part are detected, and structure of the observation object is analyzed based on detection result obtained by the detection part. At this time, a signal electromagnetic wave and a reference electromagnetic wave are detected as the outputted electromagnetic wave changes a dipole moment of an induction factor included in the observation object. Positive change in the dipole moment of the induction factor in the observation object by the electromagnetic waves leads to change in dipole moment of induction, factor in the observation object during irradiation with the electromagnetic wave, thereby changing distribution of dielectric constant in the observation object. Accordingly, at a boundary part in the observation object where a medium changes, if an induction factor is included in any one of both sides sandwiching the boundary part, the change in the dipole moment of the induction factor leads to change in a dielectric constant of a medium at the side including the induction factor. For that reason, it is possible to create and positively increase a difference between values of distribution of dielectric constant of the mediums at both sides of the boundary part. As a result, the electromagnetic wave is accurately reflected at the boundary part of the medium, in the observation object. Therefore, it will be possible to obtain information about the boundary part etc of the medium in a clearer state by detecting a signal electromagnetic wave coming through the observation object and a reference electromagnetic wave coming without passing through the observation object and comparing the signal electromagnetic wave and the reference electromagnetic wave. For example, if the reference electromagnetic wave is used as a standard, it is possible to obtain, information about the boundary part etc of the medium in a clearer state based on, for example, extent of the change in the signal electromagnetic wave occurred by passing through the observation object.

For instance, by way of example, detection by the detection part of the signal electromagnetic wave passing through the observation object will be described. The signal electromagnetic wave detected by the detection, part includes one or several reflected wave component reflected once or several times (for example, even number of times) at the boundary part of the medium on or inside the observation object. In association with the increase in path, length occurred by the reflection, the reflected wave component changes its phase when, it enter the detection part. Therefore, detection of information about phase difference between a phase of the reference electromagnetic wave and a phase of the reflected wave component included in the signal electromagnetic wave allows for detection of, for instance, a distance along incident direction of the electromagnetic wave and between the boundary part of the medium in the observation object and a surface of the observation object, or a distance along incident direction of the electromagnetic wave and between boundary parts of the medium in the observation object etc based on the information about that phase difference.

As an another example, detection by detection part of a signal electromagnetic wave returning to an outputting side of the output part after being reflected at the boundary part of the medium within the observation object will be described. In this case, the signal electromagnetic wave detected by the detection part includes one or several reflected, wave component reflected once or several times (for example, odd number of times) at the boundary part of the medium on or inside the observation object. In this case, due to the increase in path length occurred by the reflection, the reflected wave component also changes its phase when it enters the detection, part. Therefore, detection of information about phase difference between a phase of the reference electromagnetic wave and a phase of the reflected wave component included in the signal electromagnetic wave allows for detection of, for instance, a distance along incident direction of the electromagnetic wave and between the boundary part of the medium in the observation object and a surface of the observation object, or a distance along incident direction of the electromagnetic wave and between boundary parts of the medium in the observation object etc, based, on the information about that phase difference. Furthermore, if several reflected wave components are included in the signal electromagnetic wave, it is found that reflected wave components with more phase lag returns after being reflected on a reflecting surface of the deeper boundary part etc along the incident direction from a face of the observation object on which the electromagnetic wave enters. For that reason, it is possible to obtain information about a location (for example, depth etc) of the reflecting surface reflecting the electromagnetic wave, i.e. such as a boundary part, with reference to the face etc of the observation object on which the electromagnetic wave enters. Furthermore, it is also possible to obtain information about for example, shape, size and so on of boundary part etc of the medium in any cross section of the observation object based on the obtained information.

As an another example, by obtaining information about strength of the signal electromagnetic wave based on strength of the reference electromagnetic wave on the basis of detection result of the both waves, it is also possible to obtain information about the boundary part of the medium in the observation object based on the detection result. For example, if an area (e.g. an object) different in medium from surroundings is present in the observation object, an incident electromagnetic wave is reflected at the surface of said area (boundary part of a medium). Thus, in a part including said area in the observation object viewed from an electromagnetic wave-irradiating side, the impact of the reflection on the surface of said area will decrease strength of the signal electromagnetic wave exiting from the observation object to the opposite side of the irradiating side, and increase strength of the signal electromagnetic wave exiting from the observation object to the irradiating side, as compared to the other parts without containing said area. Therefore, it is possible to obtain information about shape, size and so on of the area (e.g. an object) viewed from the electromagnetic wave-irradiation side, which is different in medium present in the observation object from surroundings, by using strength of the reference electromagnetic wave as a standard and examining strength distribution of the signal electromagnetic wave exiting from the observation object to the irradiating side to the opposite side of the irradiating side in the case of looking from the irradiating side.

As an another example, it is also possible to obtain information about shape, size and so on of the area (e.g. an object) viewed from the electromagnetic wave-irradiating side, which is different in medium present in the observation object from surroundings, based on distribution of strength of the signal electromagnetic wave exiting from the observation object to the irradiating side or to the opposite side of the irradiating side, without utilizing the reference electromagnetic wave.

In the above-described aspect relating to the observation device, an electromagnetic wave outputted by the output part is a pulsed laser light which is a coherent light. Accordingly, it is possible to effectively change a dipole moment of an induction factor included, in the observation object by the laser light outputted by the output part in conjunction with phase of the laser light, thereby allowing for effective change in distribution of dielectric constant in the observation object.

Since the laser light outputted by output part is a pulsed laser light continually outputted in pulses, it is possible to enhance the strength (amplitude) of each pulse of the light while controlling an output level of the pulsed laser light per unit time. This can effectively change the dipole moment of the induction factor by allowing large amplitude electromagnetic wave from the pulsed laser light to act on the induction factor when the light enters the observation object. Furthermore, impact on the observation object by the irradiation of the pulsed laser light can be controlled, since output level of the light per unit time is controlled.

In addition, shortening pulse duration of the pulsed laser light can lead to increase in width of pulse wavelength (band width) according to the uncertainty principle. If information about cross sectional structure along irradiation direction of pulsed laser light in the observation object is obtained based on phase difference etc between a reflected light of the pulsed laser light with which the observation object is irradiated and a reference light with which the object is not irradiated, increase in width of pulse wavelength (band width) of the pulsed laser light can improve resolution, in said irradiation direction, of the cross section of the observation object.

Regarding the above-mentioned aspect of the observation device, it has been found by the present inventors' research that if a wavelength of an electromagnetic wave outputted by the output part is set to a value within absorption wavelength regions of the induction factor where the electromagnetic wave, with which the induction factor was irradiated, is absorbed, by the induction factor, the irradiated electromagnetic wave can cause the induction factor to effectively induce change in the dipole moment of the induction factor. In other words, it is found that the induction factor is irradiated, with an electromagnetic wave with a wavelength where absorption of the electromagnetic wave by induction factor does not occur, no effective change in the dipole moment of the induction factor happens. This is because it is believed that the change in dipole moment of the induction factor by the electromagnetic wave irradiation is a kind of quantum state change, and that when the change in the dipole moment happens a portion of the electromagnetic wave is absorbed by the induction factor and its absorbed electromagnetic wave energy is converted into the change in the dipole moment.

Before the relationship between electromagnetic wave absorption feature of this induction factor and a wavelength, of an electromagnetic wave for observation, was found, combinations of a wavelength of an electromagnetic wave and an induction factor had been determined through troublesome trial and error. The revealed relationship between the electromagnetic wave absorption feature of this induction factor and a wavelength of an electromagnetic wave for observation can be utilized to easily determine preferable combinations of a wavelength of an electromagnetic wave and a type of an induction factor.

Furthermore, since absorption feature of the induction factor to the electromagnetic waves with each wavelength can be measured with relative ease, selection of the induction factor can be advantageously made.

In the above-mentioned aspect relating to an observation method of the present invention, not only the substantially same effect, as in the above-mentioned aspects relating to the observation device can be obtained but also the following effect can be achieved. That is, an induction factor whose dipole moment changes after induction with an electromagnetic wave is introduced into the observation object in a step of introducing the induction factor. Accordingly, an induction factor is introduced into a particular part to be observed in the observation object (e.g. a portion of a medium, structure and so on) so that information about structure of that part can be obtained in a clearer state.

DETAILED DESCRIPTION OF THE INVENTION

Figure 1:
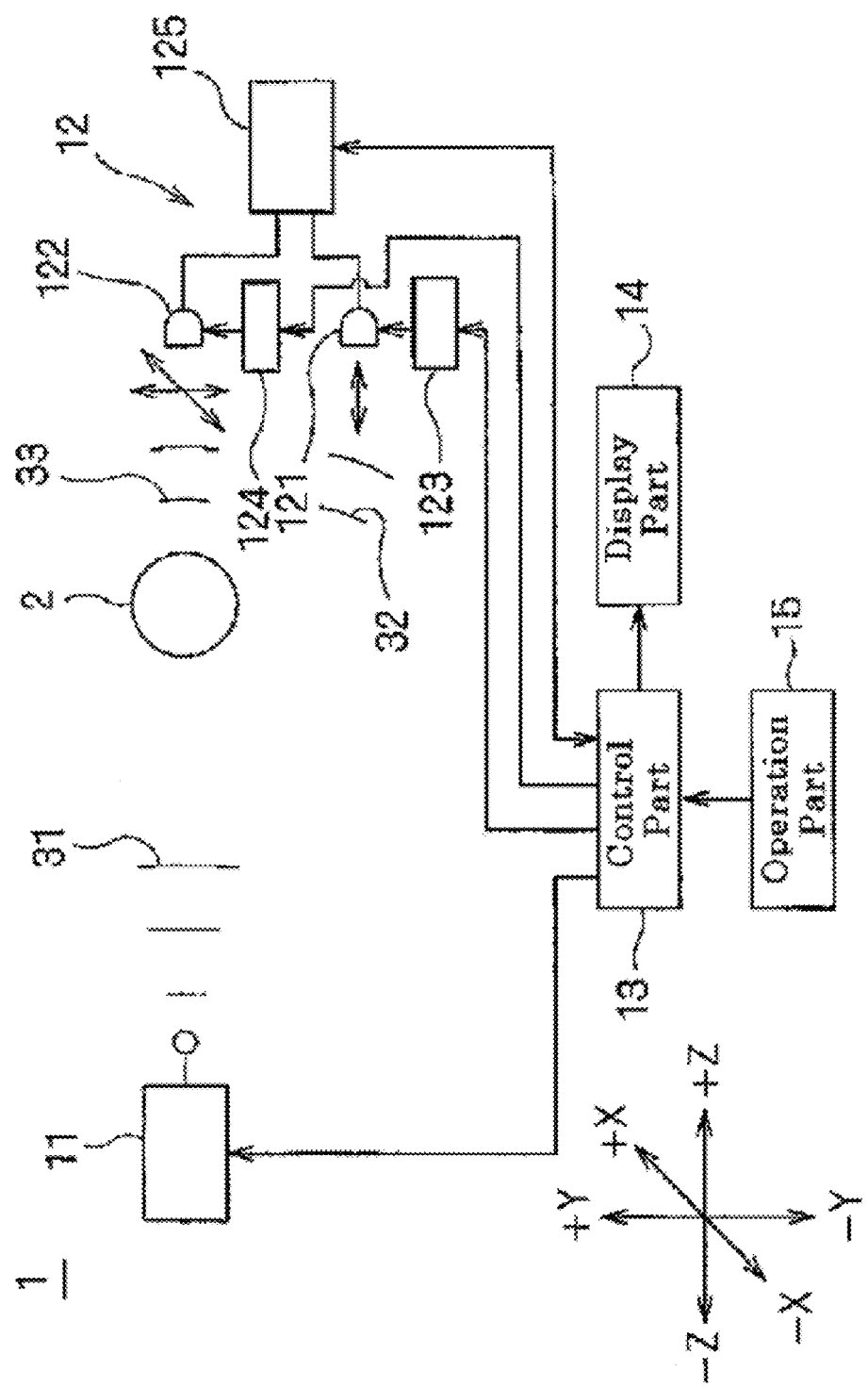
FIG. 1 It is a block diagram showing a configuration of an observation device according to an embodiment of the present invention.

An observation device according to an embodiment of the present invention will be set forth with reference to FIG. 1. An observation device 1 according to the embodiment comprises an output part 11, a detection part 12, a control part 13, a display part 14, and an operation part 15, as shown in FIG. 1, and is used for observing structures in the observation object 2. The control part 13 mainly corresponds to an analysis part of the present invention. Furthermore, the control part 13 has some roles in detection etc of phase difference between a reference electromagnetic wave 32 and a signal electromagnetic wave 33 described below. In addition, in the present embodiment and drawings, Z direction substantially corresponds to a front direction directing from the output part 11 to the side of observation object 2, a direction toward, which the electromagnetic wave is irradiated, a direction toward which the electromagnetic wave enters the observation object 2, or a direction toward which the electromagnetic wave passing through the observation object 2 or being reflected at the observation object 2 arrives when viewed from the detection part 12. X and Y directions are vertical, to the Z direction and also vertical to each other, The observation object 2 consists of a plurality of mediums and at least any one of the mediums includes an induction factor whose dipole moment changes by induction with the electromagnetic wave. This induction factor may be positively introduced into the medium prior to or during observation, while it may be included in normal state in the medium of the observation object 2. A concrete example of the induction factor includes, for instance, a physiologically active substance etc.

When the induction factor is positively introduced into the observation object 2, this step is called as an induction factor introduction stage, and a step of observing internal structure of the observation object 2 by irradiating the observation object 2 with the electromagnetic wave from the output part 11 is called an observation stage. Introduction of the induction factor in this introduction stage includes a method of introducing the induction factor into the observation object 2 by immersion, for instance, through surface of the observation object 2 or through a gap between several mediums appeared on the surface. In this case, it is possible to employ a method of soaking the observation object 2 in a liquid induction factor or a method of spraying or applying the liquid induction factor on the surface of the observation object 2. Furthermore, another methods of introducing the induction factor include a method of injecting the liquid induction factor into the observation object 2. In this case, it is also possible to employ a method of injecting the liquid induction factor into a given site (e.g. a given medium, or internal structure) in the observation object 2 by using a given injection tool and so on.

Figure 2:
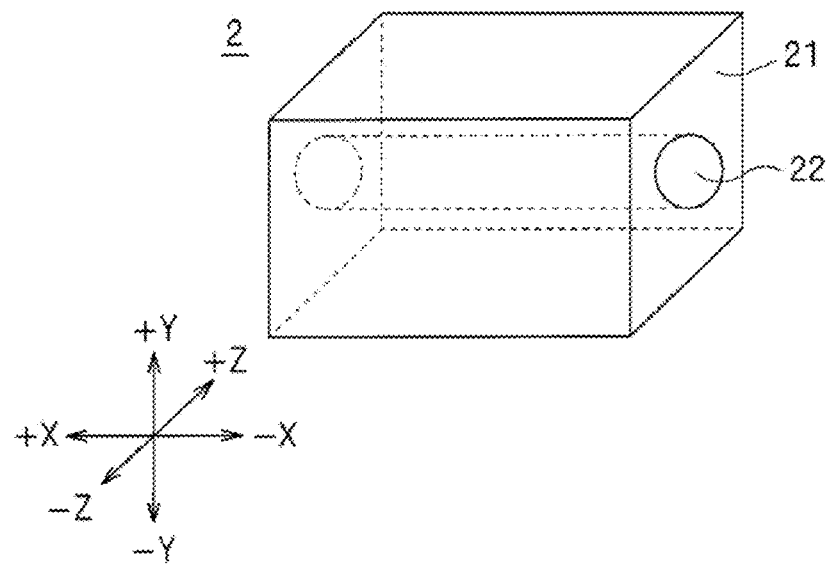
FIG. 2 It is a perspective view showing a configuration of the observation device included by way of example.

A concrete example of the observation object 2 includes the one shown in FIG. 2, by way of example. The observation object 2 in FIG. 2 consists of a medium 21 to form a fundamental structure of the observation object 2 and a medium 22 present so as to be embedded in the medium 21. Said induction factor is included, for instance, in the medium 22. Observation of the observation object 2 in this FIG. 2 observes shape, size and so on of an area, including the medium 22 inside the observation object 2.

The output part 11 outputs an electromagnetic wave 31 toward the direction (+Z direction) of installed, observation object 2 under the control by the control part 13 and changes the dipole moment of the induction factor included in the observation object 2 by the outputted electromagnetic wave 31. Concrete content of the electromagnetic wave 31 outputted by the output part 11 will be described below.

The detection part 12 detects among the electromagnetic waves 31 outputted by the output part 11 a reference electromagnetic wave 32 coming without passing through the observation object 2 and a signal electromagnetic wave 33 coming through the observation object 2. More particularly, the detection part 12 comprises a first detection unit 121, a second detection unit 122, a first driving part 123, a second driving part 124, and a signal processing part 125.

The first detection unit 121 is placed along Z direction at a position opposed to the output part 11 across the observation object 2. The first detection unit 121 detects the reference electromagnetic wave 32 under the control of the control part 14, converts the detected reference electromagnetic wave 32 into an electrical signal (a first detection signal), and transmits the signal to the signal processing part 125. The second detection unit 122 is placed at a position so as not to hide behind the observation object 2 when the observation object 2 is viewed from the output part 11 which is located closer to +Z direction than the observation object 2 is. The second detection unit 122 detects the signal electromagnetic wave 33 under the control of the control part 14, converts the detected signal electromagnetic wave 33 into an electrical signal (a second, detection signal), and transmits the signal to the signal processing part 125. The electromagnetic wave 31 outputted by the output part 11 then propagates extending outwardly. For that reason, a portion of the electromagnetic wave 31 also enters the first detection unit 121 placed, at a position deviated from an output axis of the electromagnetic wave 31 outputted by the output part 11. A more concrete configuration of the first and second detection units 121, 122 is composed of, for example, a receiving antenna, a receiving circuit, and so on.

Figure 3:
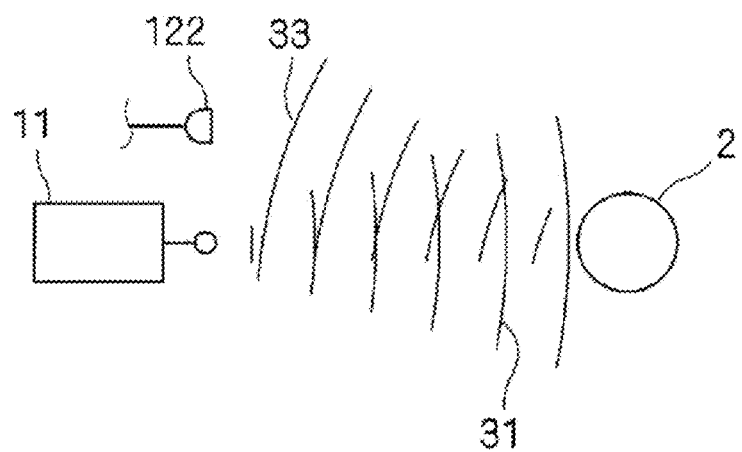
FIG. 3 It shows a configuration of a portion of a variation of the observation device according to claim 1.

In the configuration in FIG. 1, the second detection unit 122 is placed at a position opposed to the output part 11 across the observation object 2. The second detection unit 122 detects as the signal electromagnetic wave 33 the electromagnetic wave 31 which transmitted the observation object 2 toward the opposite side of the irradiation side, i.e. the output 11 (−Z direction), among the electromagnetic waves 31 entering the observation object 2 after being outputted by the output part 11. As a variation example regarding this, the second detection unit 122 may be placed at the electromagnetic wave 31-irradiating side (−Z direction) viewed from the observation object 2, where the output part 11 is placed, as shown in FIG. 3. In this case, the second detection unit 122 detects as the reference electromagnetic wave 32 the electromagnetic wave 31 reflected at the observation object 2 in −Z direction, among the electromagnetic waves 31 entering the observation object 2 after being outputted by the output part 11. In this case, the first detection unit 121 may also be placed in −Z direction to the observation object 2. In this case, the electromagnetic waves 31 outputted by the output part 11 may be reflected by a reference object, which reflects an electromagnetic wave, to enter the first detection unit 121.

Additionally, the first detection unit 121 is movably placed along Z direction. A first driving part 123 moves the first detection unit 121 along Z direction under the control of the control part 13. This allows path length of the electromagnetic wave 31 to change until the wave 31 is outputted by the output part 12 and detected by the first detection unit 121. For instance, as described below, information about phase difference between the reference electromagnetic wave 32 and the signal electromagnetic wave 33 can be easily obtained by moving the first detection unit 121 along Z direction by the first driving part 123 and detecting relative position change etc of phases of the both waves 32, 33.

A variation example regarding this may allow the second detection unit 122, instead of the first detection unit 121, to move along Z direction and allow the second detection unit 122 to move along Z direction, by a second driving part 124 described below. In this case, the first driving part 123 may be omitted.

Furthermore, the second detection unit 122 is placed to be independently movable along each, of X and Y directions. The second driving part 124 allows the second detection unit 122 to independently move along each of X and Y directions under the control of the control part 13. This can lead to acquisition of information about the structure of the observation object 2 viewed from −Z direction at any position in X and Y directions. As a variation example relating to this, the second detection unit 122 may be moved along only one of X or Y directions by the second driving unit 124.

When the electromagnetic wave 31 is detected before the observation object 2 is placed (a standard setting state), the first detection unit 121 and the second detection unit 122 are set to be substantially equal to each other. In this standard setting state, for example, path length from the first detection unit 121 to the output part 11 and path length from the first detection unit 121 to the output part 11 are set to be substantially equal. This position of the first detection unit 121 is regarded as a standard setting position.

The signal processing part 125 processes and detects a first and a second signals given from the first and the second detection units 121 and 122 under the control of the control part 13, and provides the result to the control part 13. For instance, the signal processing part 125 may be incorporated with an operational amplifier and perform a variety of arithmetic processing for the first and the second signals.

The control part 13 controls the observation device 1 and analyzes structure of the observation object 2 based on the detection result of the reference electromagnetic wave 32 and the signal electromagnetic wave 33 by the control part 12. The display part 14 displays operation information for operating the observation device 1, images etc about the structure of the observation object 2 etc by the control part 13. An example of the images displayed by the display part 14 includes, for example, images showing cross-sectional structure of the observation object 2 (e.g. boundary part 23a, 23b of the below-described, mediums 21, 22). The operation part 15 receives operational input for the observation device 1.

Next, action of the observation device 1 (in particular, the control part 13) and the way to obtain the information about the structure of the observation object 2 by using the observation device 1 will be set forth below. The induction factor may be introduced into a part of the observation object 2 (e.g. any mediums 21, 22) before for during) observation of the observation object 2 by the observation device 1.

In this observation device 1, the electromagnetic wave 31 is outputted to the observation object 2 by the output part 11 and the reference electromagnetic wave 32 and the signal electromagnetic wave 33 are detected by the first and second detection unit 121, 122 of the detection part 11, respectively. The detection result, i.e. the first and the second detection signals, is sent to the signal processing part 125 and the signal processing part 125 processes the first and the second detection signals. This processing by the part 125 includes mixing the first and the second signals, correlation processing (e.g. multiplication), detection of strength of each, detection signal, or detection of the strength differential. The results of the processing by the signal processing part 125 is given to the control part 13 and used for analysis of the structure of the observation object 2 and for generation of the display images about the structure.

In terms of the detection of the electromagnetic waves 32 and 33, the reference electromagnetic wave 32 and the signal electromagnetic wave 33 are detected, with the dipole moment of the induction factor included in the observation object 2 changed during the detection. Thus, this positive change by the electromagnetic wave 31 of the dipole moment of the induction factor in the observation object lead to the change in distribution of the dielectric constant in the observation object 2. Accordingly, for instance, if the induction factor is included in the medium 22, the change in the dipole moment leads to change in dielectric constant, i.e. refractive index of the medium 22. Therefore, this can positively create or increase difference of values of dielectric constant of the mediums 21, 22 on both sides of the boundary part, therebetween. As a result, the electromagnetic wave would be precisely reflected at the boundary part of the mediums 21, 22.

For that reason, comparing the first and the second detection, signals obtained, from detection of the reference electromagnetic wave 32 and the signal electromagnetic wave 33 enables obtaining information about the boundary part etc of the mediums 21, 22 in a clearer state. For instance, based on extent of the change in the reference electromagnetic wave 33 occurred by passing through the observation object 2, as compared to the reference electromagnetic wave 32 as a standard, the same information can be obtained in a clearer state.

Next, preferred examples of the electromagnetic wave 31 used for observation of the observation object 2 will be concretely set forth.

Firstly, the electromagnetic wave 31 needs to be a coherent electromagnetic wave. This is because if phases of the electromagnetic wave 31 are not equal, electromagnetic field associated with the electromagnetic wave 31 entering the observation object 2 would act on the induction factor in the observation object in the different phases and thus the electromagnetic wave 31 would non-uniformly act on the dipole moment of the induction factor, which could not create any effective change in the dipole moment. Using a coherent electromagnetic wave as the electromagnetic wave 31 could effectively change the dipole moment in conjunction with the phase of the electromagnetic wave, thereby effectively changing distribution of the dielectric constant in the observation object 2.

An electric wave (e.g. a microwave etc), which has longer wavelength than light and is generated by antenna, is coherent in a normal state unless it is positively scattered such as through an interference grating. If the light is used as the electromagnetic wave 31, however, a coherent light, i.e. a laser light, should be used.

Furthermore, wavelength of the electromagnetic wave 31 is preferably set to a value within an absorption wavelength region where the electromagnetic wave is absorbed by the induction factor in the observation object 2. In other words, it is preferable to select the induction factor so as to include within the effective absorption wavelength region the electromagnetic wave 31 outputted by the output part 11 and to introduce the factor into the observation object 2.

This is because the inventors' research revealed, that if the electromagnetic wave 31 to irradiate the observation object 2 with is set to a value within an absorption wavelength region of the induction factor in the observation object 2, the irradiated electromagnetic wave 31 could cause the induction factor to induce the change in the dipole moment. In other words, even, if the induction factor is irradiated with am electromagnetic wave with a wavelength outside the absorption wavelength region, it does not absorb the electromagnetic wave nor effectively change the dipole moment thereof. By way of principle explanation of this, since the change in the dipole moment of the induction factor by irradiation with the electromagnetic wave 31 is a type of a quantum state change, it is thought that a portion of irradiated electromagnetic wave 31 is absorbed by the induction factor during the change in the dipole moment and energy of that absorbed electromagnetic wave 31 is converted into the change in the dipole moment. For that reason, it is thought that, even if an electromagnetic wave 31 with a wavelength at which no absorption is generated, no change in the dipole moment will occur.

For wavelength of the electromagnetic wave 31, when the induction factor included in the observation object 2 is irradiated with the electromagnetic wave 31, absorbance of the electromagnetic wave 31 by the induction factor is preferably set within a range of effective absorption wavelength, such as, beyond a certain lower limit reference level and below a certain upper limit reference level. When incident strength of the electromagnetic wave 31 with which the induction factor is irradiated is set to Iin and transmission strength is set to Iout, Absorbance (Abs) is dimensionless quantity given, by a formula:

$$Abs=-\log(Iout/Iin)$$

The log above is a common logarithm.

The reason to set the above-mentioned lower limit (lower limit reference level) of the range of effective absorption wavelength is that if no absorption beyond a certain level of the electromagnetic wave by the induction factor is generated, no change in the dipole moment of the induction factor enough to result in effective change in distribution of dielectric constant in the observation object 2 can be obtained. In addition, the reason to set the upper limit of the range (upper limit reference level) of effective absorption wavelength is that if absorbance of the electromagnetic wave 31 by the induction factor becomes larger than necessary, out of the electromagnetic waves 31 with which the observation object 2 is irradiated, a ratio of the electromagnetic wave 31 to be absorbed increases too much, and strength of the electromagnetic wave (a transparent wave or a reflected wave) obtained by the observation object 2 for observation decreases too much, thereby reducing detection accuracy. The lower limit reference level of the effective absorption wavelength region is set to, for instance, about 0.22 (e.g. 0.22) and the upper limit is set to, for instance, about 3 (e.g. 3).

Before, this relationship between the electromagnetic wave absorption feature of the induction factor and the wavelength of the electromagnetic wave 31 for observation was revealed, it had taken troublesome trial and error to determine a combination of the wavelength of the electromagnetic wave 31 and a type of the induction factor. However, utilizing this relationship, the combination of the wavelength of the electromagnetic wave 31 and an induction factor's type can be easily determined.

Furthermore, since absorption feature of the induction factor for each wavelength of the electromagnetic wave 31 can be measured with relative use, it is possible to advantageously select the induction factor.

Energy of the electromagnetic wave 31 absorbed, by the induction factor is converted into not only the change in the dipole moment but also other quantum state change of thermal vibration mode etc. For that reason, it is not easy to measure if how much of the absorbed energy of the electromagnetic wave 31 is converted into the change of the dipole moment. However, the effective absorption wavelength region of the induction factor is relatively easy to examine, and thus it is possible to more effectively select a preferable combination of the wavelength of the electromagnetic wave 31 and the induction factor's type based on the absorption wavelength region.

Next, measure absorbance of the electromagnetic waves with each wavelength for some test samples, and examine if these samples can be employed as an induction factor in view of the relationship with the electromagnetic wave 31. The induction factor includes not only an inductor itself occurring electromagnetic wave induction in which the dipole moment changes by the electromagnetic wave 31, but also a solution (induction solution) in which such, a inductor is dissolved in a solvent. If the induction factor is introduced into the observation object 2, the induction solution, which is a liquid, is easy to be introduced and thus preferable.

A preferable example of the induction factor as an electromagnetic wave 31 is discussed herein when a laser light within a visible to near-infrared wavelength range is used. Selecting a visible to near-infrared wavelength range as a concrete example of a wavelength of the electromagnetic wave 31 has the technical meanings as follows. The reason for setting an upper limit of the concrete example of wavelength of the laser light used for the electromagnetic wave 31 to a near-infrared region is that if the wavelength is longer than that, resolution to obtain information about the cross-sectional structure of the observation object 2 will be reduced. In addition, if the wavelength is longer than near-infrared region, larger portion of the electromagnetic wave is absorbed in water and thus the techniques of the present invention cannot be effectively applied to observation of the observation object 2 (e.g. a biological tissue of fundus of human/s eye) containing water. Additionally, the reason for setting an lower limit of the concrete example of wavelength of the laser light used for the electromagnetic wave 31 to a visible region is that an ultraviolet light has a significant impact on the biological tissue and thus it is not preferable to observe a human tissue. Therefore, using a laser light within a visible to near-infrared wavelength region as the electromagnetic wave 31 allows for acquisition of information about cross-sectional structure etc of the observation object 2, such as a biological tissue, with advantageous resolution. If a wavelength region of the laser light used for the electromagnetic wave 31 is numerically shown, it would be equal to or more than about 360 nm (e.g. more than 360 nm) and equal to or less than 2.5 μm (e.g. less than 2.5 μm).

As a test sample, Brilliant Blue solution containing Brilliant Blue FCF ($C_{37}H_{34}N_2Na_2O_9S_3$) dissolved in water, Pentacene solution containing Pentacene ($C_{22}H_{14}$) dissolved in ethanol, Indocyanine Green (hereinafter referred to as ICG) solution containing Indocyanine Green dissolved in water, and water were used. Indocyanine Green is approved for use in human body and has small impact on a living body when it is introduced into a living tissue of a human's body etc, it is therefore effective for observation of a biological tissue.

The reason for including water as a test sample is to use electromagnetic wave induction effect (an effect of changing dipole moment by induction with an electromagnetic wave) of water, a main component of a biological tissue, as a standard. In short, if a biological tissue is selected as the observation object 2, an induction factor needs to produce more preferable electromagnetic wave induction effect than water in order to effectively function. From this viewpoint, if a biological tissue is used as the observation object 2, what is necessary to an induction factor is that a dipole moment (or dielectric constant) of the induction, factor needs to change more than a dipole moment (or dielectric constant) of water toward the electromagnetic wave 31 (e.g. a laser light with a certain wavelength) changes.

Figure 5:
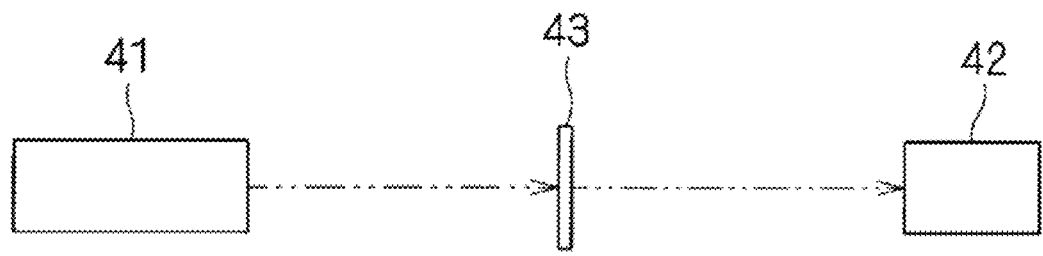
FIG. 5 It is an explanatory diagram showing an aspect of measuring absorbance of each wave of a test sample to an electromagnetic wave in accordance with an Induction factor.

As shown in FIG. 5, absorbance is measured by using a light source unit 41 to be able to irradiate with a light with a certain wavelength and a light-receiving unit 42 to detect strength of an incident light. Wavelength of a light outputted by the light source unit 41 can be varied. The light source unit 41 is provided with two light-exiting ports for measurement and reference, and the light-receiving unit 42 is also provided with two light-receiving parts for measurement and reference. A quartz cell 43 containing a solution, i.e. a test sample, is placed between the light-exiting port of the light source unit 41 for measurement and the light-receiving part of the light-receiving unit 42 for measurement. An empty quartz cell 43 for reference is placed between the light-exiting port of the light source unit 41 for measurement and the light-receiving part of the light-receiving unit 42 for measurement. Then, lights with each wavelength exiting from each light-exiting port of the light source unit 41 are received through the quartz cell 43 containing a test solution and the empty quartz cell 43 for reference, respectively, at each light-receiving part of the light-receiving unit 42, respectively, and strength of the received lights is detected. Subsequently, strength of the received lights for measurement is divided by strength of the received lights for reference, which is used as a standard, and a logarithmic value of an obtained value by the division is set to be Absorbance of each wavelength. This allows for measurement of Absorbance at each wavelength of the test samples, eliminating the influence of a container (a quartz cell) etc to retract the samples.

Figure 6:
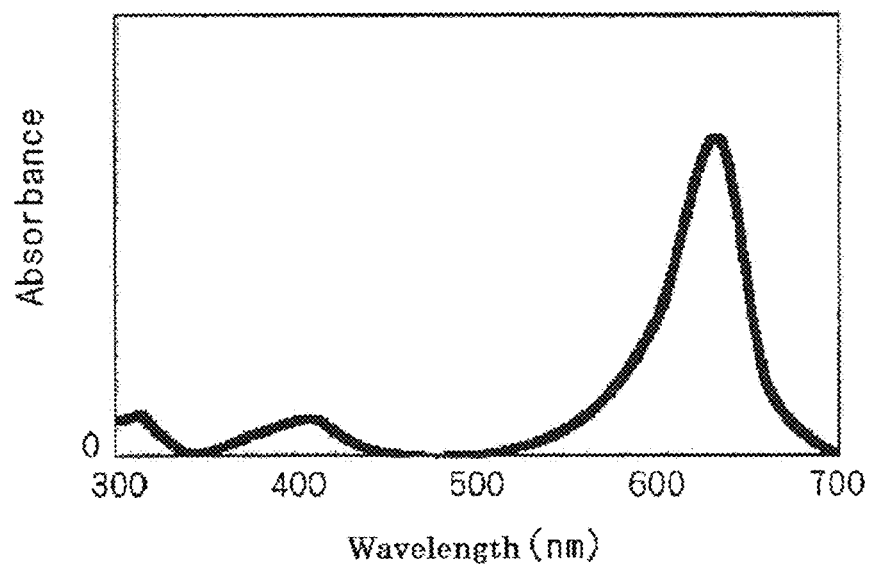
FIG. 6 It is a graph showing absorption wavelength spectrum of a brilliant blue solution.
Figure 7:
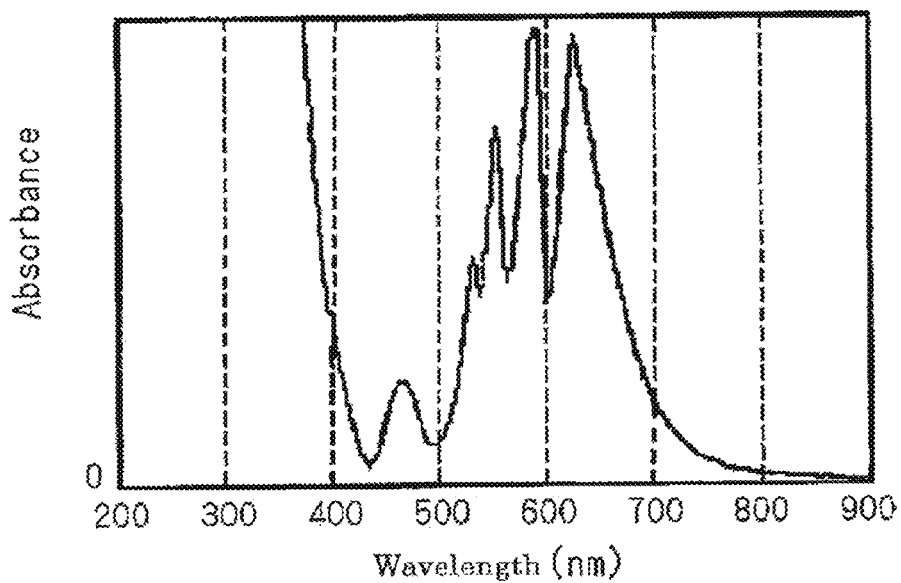
FIG. 7 It is a graph showing absorption wavelength spectrum of a pentacene ethanol solution.
Figure 8:
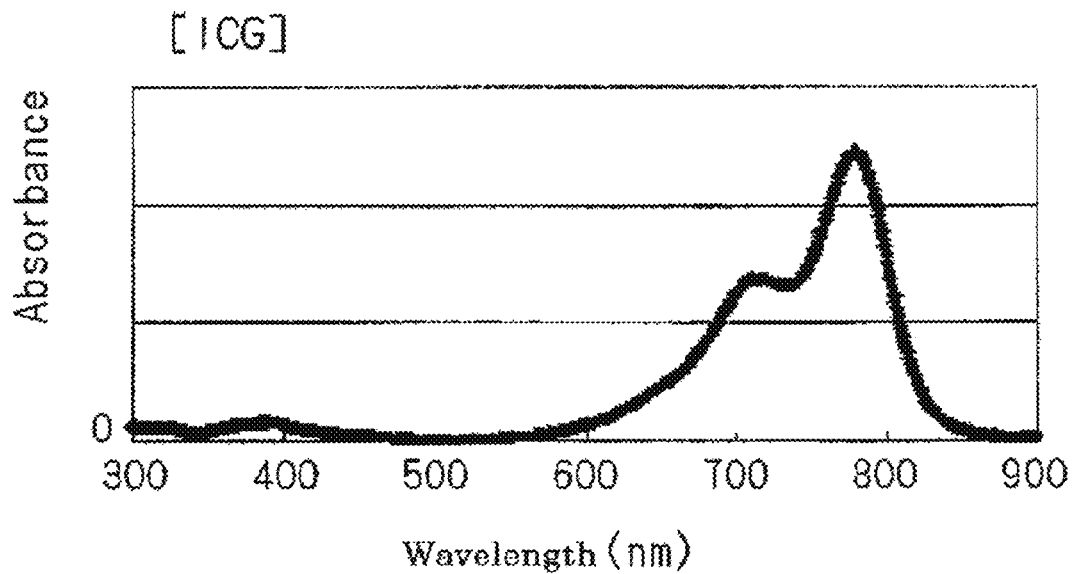
FIG. 8 It is a graph showing absorption wavelength spectrum of an indocyanine blue solution.
Figure 9:
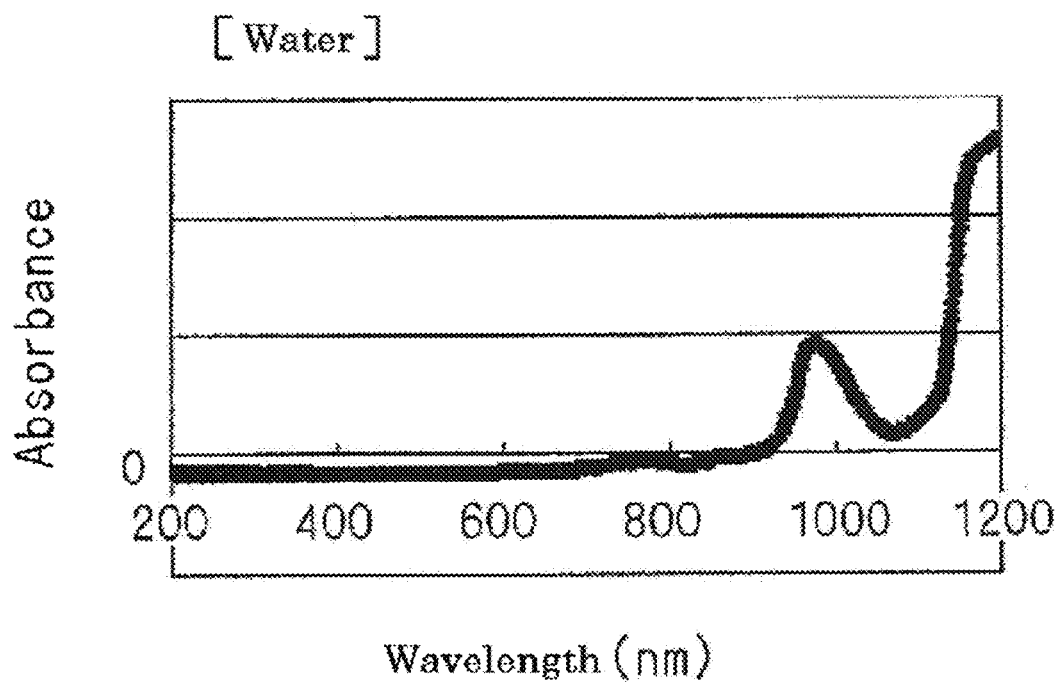
FIG. 9 It is a graph showing absorption wavelength spectrum of water.

FIGS. 6 and 9 are graphs showing measurement results (absorption wavelength spectrum) of absorbance of each test samples. Horizontal axis represents wavelength of irradiated, lights, and vertical axis represents absorbance of each wavelength. Furthermore, FIG. 6 shows absorption wavelength spectrum of a brilliant blue solution, FIG. 7 shows absorption wavelength spectrum of a pentacene ethanol solution, FIG. 8 shows absorption, wavelength spectrum of an ICG solution, and FIG. 9 shows absorption wavelength spectrum of water. Concentration of a medium, such as ICG, to be dissolved in each solution is not specifically limited. If high electromagnetic wave induction effect (extent of change in a dipole moment by induction with an electromagnetic wave) based on a solute, such as ICG etc, is desired, concentration of the solute is preferably set higher. Conversely, if low electromagnetic wave induction effect is desired, the solute concentration is preferably set low. However, if a biological tissue etc is used as the observation object 2, the solute concentration should be set in view of the impact on the human tissue.

According to the measurement result in FIG. 6, it is found that the above-mentioned effective absorption wavelength region regarding the brilliant blue solution is in the range of, for example, about 500 nm to about 750 nm. According to the measurement result in FIG. 7, it is found that the effective absorption, wavelength region regarding the pentacene ethanol solution is in the range of, for example, about 430 nm to about 880 nm. According to the measurement result in FIG. 8, it is found that the above-mentioned effective absorption wavelength region regarding the ICG solution is in the range of, for example, about 500 nm to about 950 nm. According to the measurement result in FIG. 9, it is found that the effective absorption wavelength region of water is in the range of, for example, about 900 nm to about 1050 nm, and in the range of, for example, 1120 nm to 1300 nm, and that there are some absorption wavelength regions in infrared region. Additionally, measurement result in FIG. 9 reveals that since absorption wavelength region of water is distributed more over long-wavelength side than, visible region, absorption wavelength features in the visible region of the brilliant blue solution and the ICG solution mainly depends on impact of solutes, i.e. the brilliant blue and the ICG. Furthermore, since it is known that ethanol does not have absorption wavelength region in the visible region, absorption wavelength features in the visible region of the pentacene ethanol solution mainly also depends on impact of the pentacene.

Concretely identify wavelength of a light (a laser light) used as the electromagnetic wave 31 for observation and then examine which of the above-mentioned four types of test samples is preferable as an induction factor. For example, wavelength of a laser light is set about 800 nm, it is clear that the ICG solution contains wavelength of 800 nm near the center of effective absorption wavelength region and thus is most preferable for an induction factor. It turns out that the pentacene ethanol solution also has the wavelength of 800 nm even at a bottom part of the effective absorption wavelength region and thus is usable for an induction factor. In addition, it turns out that the brilliant blue solution and water do not have the wavelength of 800 nm in that effective absorption wavelength region, and thus they are difficult to use as an induction factor. In association with this point, a test was conducted by using an optical coherence tomography as shown FIG. 12 and its result will be described below.

Promising materials for an induction factor will be described below. First, these materials include biologically active substances such as a aye (including an organic dye and an inorganic dye). A variety of dyes are already known and many of them have absorption wavelength region to absorb a light into a visible to infrared wavelength region. For that reason, by using a dye as an induction factor, it is possible to increase flexibility of a combination of wavelength of the electromagnetic wave for observation and dyes used for induction factor. Using an organic dye for an induction factor produces a benefit that many organic dyes present in biological tissues can be utilized. Other biologically active substances include, for instance, protein, cholesterol, fat globule, lipid, erythrocyte, leukocyte, platelet and so on. In addition to these, an induction factor includes water, ice, alcohol, glass, quartz, diamond, plastic, semiconductor, and so on. However, relationship between absorption wavelength features of these materials and wavelength of the electromagnetic wave for observation must satisfy the condition described above.

Furthermore, a laser light used for the electromagnetic wave 31 is preferably a pulsed laser light continuously outputted in pulses.

Using a pulsed laser light (e.g. an ultra-pulsed laser light) continuously outputted in pulses as the electromagnetic wave 31 increases strength of each pulse of a pulsed laser light, while controlling output level of the pulsed laser light per unit time. This causes the electromagnetic wave with large-amplitude due to the laser light to react to the induction factor in the observation object 2 when the pulsed laser light enters the observation object 2, thereby effectively changing the dipole moment of the induction factor. Furthermore, since output level of the pulsed laser light per unit time is controlled, the impact of the irradiation of the pulsed laser light on the observation object 2 can be controlled.

Also, a pulse wavelength width (a bandwidth) can be broadened based on the uncertainty principle by shortening a pulse time width of the pulsed laser light. In case of obtaining information about a cross-sectional structure along a direction of irradiation with the pulsed laser light within the observation object 2 based on such as a phase difference between a reflected light of the pulsed laser light with which the observation object 2 was irradiated and a reference light which did not pass through the observation object 2, a resolution of the cross-sectional surface of the observation object 2 to said irradiation direction can be improved by broadening the pulse wavelength width (the bandwidth) of the pulsed laser light.

Moreover, in case that the structure within the observation object 2, etc. temporally changes, information about the structure within the observation object 2, etc. which temporally changes can be obtained, at stroboscopecaliy short time interval (an intermittent cycle) by intermittently chopping the pulsed laser light, which is outputted continuously at a predetermined pulse cycle, at bigger intermittent cycle than the pulse cycle and irradiating the observation object 2 with the pulsed laser light.

A pulse time width of the pulsed laser light used as an electromagnetic wave 31 is preferably shorter than a duration from an entry of the pulsed laser light into the observation object 2 to an emission of the electromagnetic wave in connection with a state transition of an induction factor within the observation object 2 excited by the pulsed laser light. The pulse time width here is so-called a full width at half maximum (FWHM), that is, a width of a pulse waveform which is cut along a horizontal axis at a half value point of the peak value. Below-mentioned pulse wavelength width is also called FWHM as well.

For this reason, the pulse time width of the pulsed laser light used is preferably shorter than the duration from the entrance of the pulsed laser light into the observation object 2 to the emission of the electromagnetic wave in connection with a state transition of an induction factor within the observation object 2 excited by the pulsed laser light (e.g., about 100 micro seconds of order). On the other hand, a change in a dipole moment of the induction factor with the pulsed laser light within the observation object 2 occurs almost simultaneously with an entry of the pulsed laser light into the observation object 2 and its timing is earlier than that in which the light is emitted m connection with the state transition of the induction factor within the observation object 2 excited by the pulsed laser light. Therefore, when the pulsed laser light enters the observation object 2, prior to the light emission in connection with the state transition of the induction factor, a dielectric constant distribution within the observation object 2 changes with a change in dipole moment of the induction factor, and the pulsed laser light affected by the change in the dielectric constant distribution exits outside the observation object 2 as a reflected light or transmitted light. As a result, information about the structure within the observation object 2 can be obtained by using the pulsed laser light without being-affected by a light emitted in connection with the state transition of the induction factor within the observation object 2 excited by the pulsed laser light.

Specifically, for example, the pulse time width of the pulsed laser light used as an electromagnetic wave 31 is preferably designated as a value of 10 or more femtoseconds (e.g., 10 or more femtoseconds) and 1 or less picoseconds (e.g., 1 or less picoseconds). That is, as a pulsed laser light used as an electromagnetic wave 31, femtosecond pulsed laser light in which the pulse time width has a scale of femtosecond is preferably used. The pulsed laser light with such an extremely short pulse time width, may be called an ultrashort pulsed laser light.

The reason that the lower limit of the pulse time width, of the pulsed laser light is designated as 10 femtoseconds is that the pulsed laser light with less than 10 femtoseconds of the pulse time width is difficult to be produced since it has a large expansion of the pulse time width by a dispersion when it passes through an optical system. In addition, the reason that the upper limit of the pulse time width is designated as 1 picosecond is that the pulse wavelength width of the pulsed laser light determined in relation to the pulse time width based on the uncertainty principle becomes too narrow as the pulse time width becomes longer than 1 picosecond and a resolution to observe a cross-sectional structure of a imaging object 2, etc. drops too low. For example, if the pulse time width of the pulsed laser light is about 10 femtoseconds, about 1 μm of the resolution or finer scale of the resolution can be expected, if about 100 femtoseconds, about 1-3 μm scale of the resolution can be expected, and if about 1 picosecond, about 10 μm or greater scale of the resolution can be expected.

Therefore, by designating the pulse time width of the pulsed laser light used as an electromagnetic wave 31 as a value of 10 or more femtoseconds and 1 or less picoseconds, a strength (amplitude) of each pulse of the pulsed laser light can be increased while controlling an output level of the pulse laser per unit time and the dipole moment of the induction factor within the observation object 2 can be effectively changed by the pulsed laser light. Additionally, information about the cross-sectional structure of the observation object 2, etc, can be obtained with a high resolution.

Figure 10:
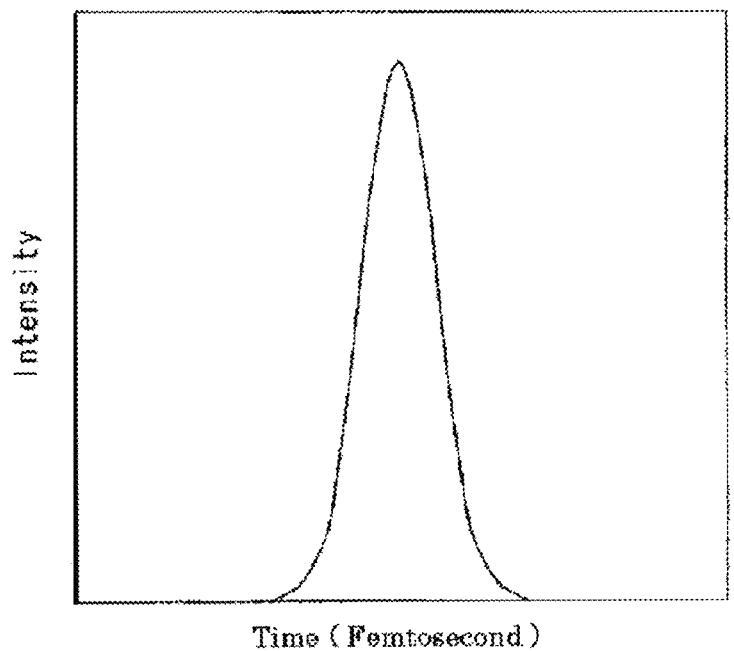
FIG. 10 It is a graph showing a pulse waveform of a pulsed laser light for observation with a horizontal axis set as time.
Figure 11:
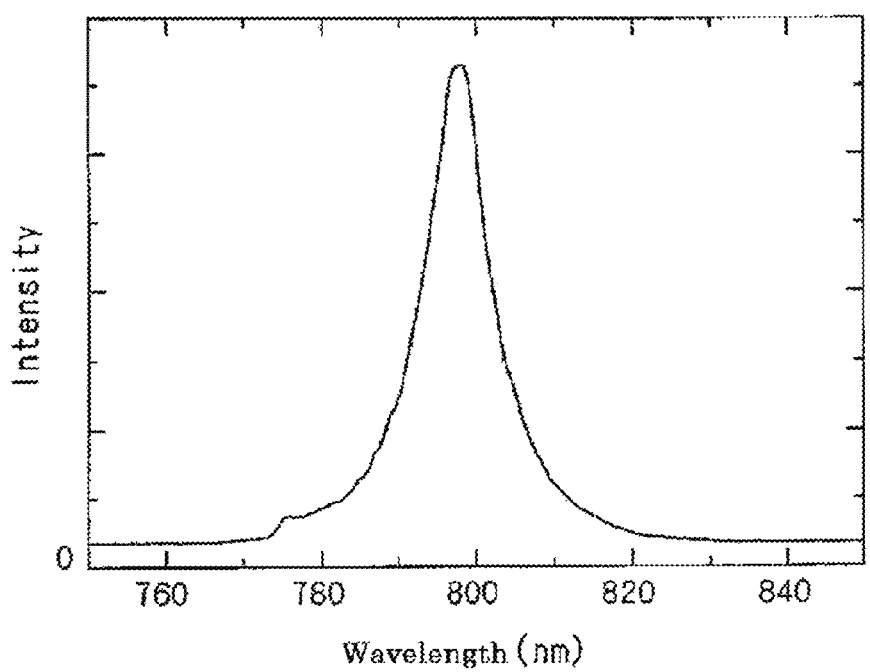
FIG. 11 It is a graph showing a pulse waveform of a pulsed laser light for observation in FIG. 10 with a horizontal axis set as wavelength.

By way of example, such pulsed laser lights include the lights in FIG. 10 and FIG. 11. The pulse time width of this pulsed laser light is about 100 femtoseconds and the pulse wavelength width is about 15 nm. And the peak wavelength of this pulsed laser light (a wavelength at the peak of the pulse waveform) is about 795 nm.

Then, referring to FIG. 4, the way the structure within the observation object 2, etc. is detected employing a change in the dipole moment of the induction factor contained in the observation object 2 by the irradiation with the electromagnetic wave 31 will be explained.

Figure 4:
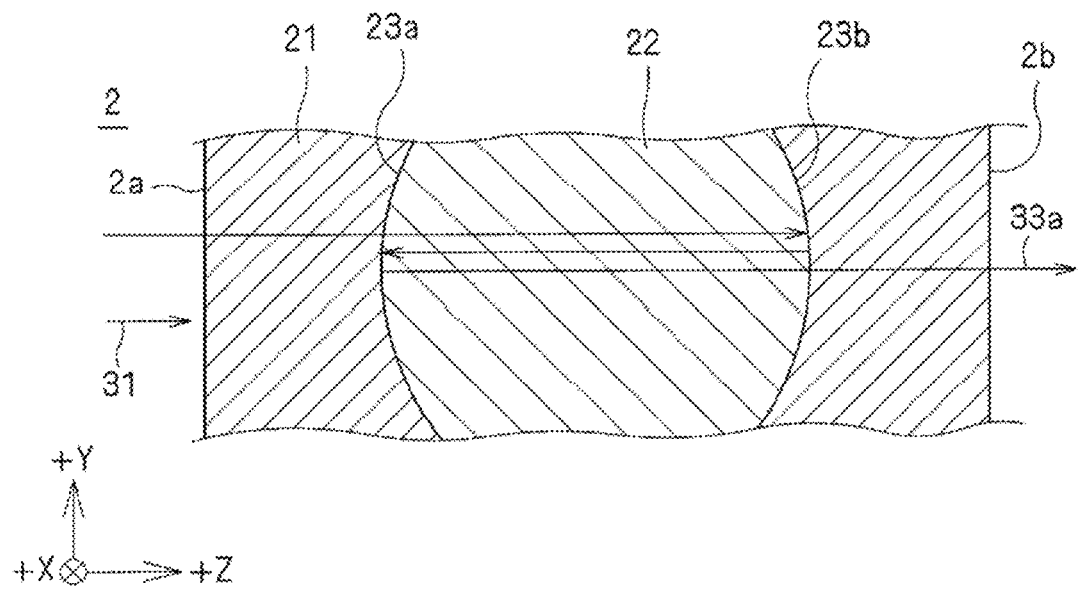
FIG. 4 It is an enlarged view showing a cross-sectional configuration of the observation object according to claim 2.

When the above-mentioned observation object 2 is irradiated with the electromagnetic wave 31, as shown in FIG. 4, the electromagnetic wave 31 can be reflected on a surface 2a, 2b of a −Z direction and +Z direction of the observation object 2, and boundary parts 23a, 23b with a medium 21 and a medium 22. Thus, as shown in FIG. 1, when a transmitted wave is detected by a second detection unit 122, a signal electromagnetic wave 33 detected by the second, detection unit 122 includes one or several reflected wave component reflected several times (e.g., even number of times) on the surface 2a, 2b of the observation object 2 or at the boundary parts 23a, 23b of its internal mediums 21, 22. The reflected wave component changes its phase when entering the second detection, unit. 122 in connection with an increase in a path length generated, by the reflection. Therefore, for example, a distance along the Z direction between the boundary parts 23a, 23b of the mediums 21, 22 within the observation object 2 and the surface 2a, 2b of the observation object 2, or a distance along the Z direction between the boundary parts 23a, 23b of the mediums 21, 22 within the observation object 2, etc. can be detected by detecting information about a phase difference between a phase in which a reference electromagnetic wave 32 enters the detection unit 121 and a phase of the reflected wave component included in the signal electromagnetic wave 33 and by using information about the detected phase difference.

For example, we explain about a case that the reflection of the electromagnetic wave 31 at the boundary parts 23a, 23b is the most prominent among the surface 2a, 2b and the boundary parts 23a, 23b of the observation object 2. In this case, a distance along the Z direction between the boundary parts 23a, 23b can be detected based on, as shown in FIG. 4, information about the phase difference between the reflected wave component 33a that exits to the +Z direction by being reflected once at a time at the boundary parts 23a, 23b, respectively (2 times in total) and the reference electromagnetic wave 32, among the reflected wave components included in the signal electromagnetic wave 33.

A detection of information about the phase difference between the reference electromagnetic wave 32 and the reflected wave component included in the signal electromagnetic wave 33 is conducted for example as follows. By moving the first detection unit 121 from the above-mentioned standard setting position to the Z direction (e.g., the +Z direction) by a first actuator 123 as detecting the reference electromagnetic wave 32 and the signal electromagnetic wave 33, a change in a processing result of a signal processing part 125, which is generated in connection with a movement of a first detection unit 121, is analyzed. For example, a combination or correlation processing of a first detection signal and a second detection signal, etc. may be conducted by the signal processing part 125. And when a signal value given from the signal processing part 125 becomes a maximum value, information about the phase difference (or a path difference)

between the reference electromagnetic wave 32 and the reflected wave component included in the signal electromagnetic wave 33 may be obtained based on a moving distance from the standard setting position of the first detection unit 121.

Furthermore, several reflected wave components with different path length may be included in the signal electromagnetic wave 33. In this case, a signal value given from the signal processing part 125 forms several times of peaks according to the number of the reflected wave component in a process of moving the first detection unit 121. Based on the moving distance from the standard setting position of the first detection unit 121 that corresponds to each peak of the signal, information about the phase difference (or a path difference) between the reference electromagnetic 2 and each reflected wave component included in the signal electromagnetic wave 33 is obtained in this case, too.

Additionally, information about the structure of the boundary parts 23a, 23b of the mediums 21, 22, etc. within the observation object 2 on the whole can be obtained by moving the second detection unit 122 to a X direction, Y direction by a second driving part 124. For example, information about the configuration of the boundary parts 23a, 23b of the mediums 21, 22, etc. in any cross-section where the observation object 2 is cut parallel to a Z direction can be obtained.

As an another example, we explain a case where the reflected wave is detected by the second detection unit 122 as shown in FIG. 3. In this case, the signal electromagnetic wave 33 detected by the second detection unit 122 includes 1 or several reflected wave components reflected once or several times (e.g., odd number of times) on the surface 2a, 2b of the observation object 2 or the boundary parts 23a, 23b of its internal mediums 21, 22. And the reflected wave component changes its phase when entering the second detection unit 122 in connection with an increase in a path length generated by the reflection. Therefore, for example, a distance along the Z direction between the boundary parts 23a, 23b of the mediums 21, 22 within the observation object 2 and the surface 2a, 2b of the observation object 2, or a distance along the Z direction between the boundary parts 23a, 23b of the mediums 21, 22 within the observation object 2, etc. can be detected by detecting information about the phase difference between the phase in which the reference electromagnetic wave 32 enters the detection unit 121 and the phase of the reflected wave component included in the signal electromagnetic wave 33 and using information about the detected phase difference.

Additionally, in a reflecting configuration, if several reflected wave components are included in the signal electromagnetic wave 33, it is found that reflected wave components with more phase lag return after being reflected on a reflecting surface of the deeper boundary parts 23a, 23b along the +Z direction from a surface 23a of the observation object 2. Therefore, it is possible to obtain information about a position (e.g., a depth, etc.) based on the surface 2a, etc. of the observation object 2 on the reflecting surface such as the boundary parts 23a, 23b where the electromagnetic wave 31 within the observation object 2 is reflected. Moreover, based on the obtained information, it is possible to obtain information about a shape, size, etc. of, for example, the boundary parts 23a, 23b of the mediums 21, 22 on any cross-section where the observation object 2 is cut.

Also, as an another example, based on the detection results of the reference electromagnetic wave 32 and the signal electromagnetic wave 33, by obtaining information about a strength of the signal electromagnetic wave 33 based on a strength of the reference electromagnetic wave 32, information about the boundary parts 23a, 23b of the mediums 21, 22 within the observation object 2 can also be obtained based on the detection results. For example, in case of the observation object 2 shown in FIG. 2, the electromagnetic wave 31 that enters within, the observation object 2 is reflected on a surface of the medium 22 (the boundary parts 23a, 23b of the mediums 21, 22). For this reason, if seeing from the −Z direction (an irradiation side of the electromagnetic wave 31) within the observation object 2, a strength of the signal electromagnetic wave 33 that exits from the observation object 2 to the +Z direction further decreases and a strength of the signal electromagnetic wave that exits from the observation object 2 to the −Z direction further increases by an effect of the reflection at the boundary parts 23a, 23b in a part where the medium 22 exists, compared to other parts where the medium 22 does not exist. Thus, information about an external form or size, etc., seen from the −Z direction, of the part within the observation object 2 where the medium 22 exists can be obtained by checking a distribution of a strength of the signal electromagnetic wave 31 exiting from the observation object 2 to the −Z direction or the +Z direction when, seen from the −Z direction, based, on the strength of the reference electromagnetic wave 32.

Also, as an another example, by checking a distribution of a strength of the signal electromagnetic wave 31 that exits from the observation object 2 to the −Z direction or the +Z direction when seen from the −Z direction without utilizing the reference electromagnetic wave 32, information about an external form or size, etc., seen from the −Z direction, of the part within the observation object 2 where the medium 22 exists can also be obtained.

Additionally, in the case of positively inducing said induction factor into the observation object 2, following effects can be obtained. That is, by inducing said induction factor into a part to be particularly obtained within the observation object 2 (e.g., a part of medium, structures, etc.), information about a structure of the part can be obtained in a clearer state.

Furthermore, in the above-mentioned observation device 1 of FIG. 1, as a configuration to detect information about a phase difference between the reference electromagnetic wave 32 and the reflected wave component included in the signal electromagnetic wave 33, a following configuration is also adoptable. That is, the signal processing part 125 may make at least one phase of the first detection signal obtained by a detection of the reference electromagnetic wave 32, and the second detection signal obtained by a detection of the signal electromagnetic wave 33 to advance or retreat at a variable adjusting width. Thus, by adjusting at least one advancing or retreating width of the phase of the first detection signal and the second, detection signal by the signal processing part 125, and by detecting a change in a relative position of the phases of the reference electromagnetic wave 32 and the signal electromagnetic wave 33, information about the phase difference between the reference electromagnetic wave 32 and the signal electromagnetic wave 33 can be readily obtained. In this configuration, the first driving part 123 to move the first detection unit 121 along the Z direction can be omitted, and a simplification of the configuration of the observation device 1 can be sought. Furthermore, in this configuration, the signal processing part 125 plays a role as a phase adjusting part according to the present invention.

A more specific movement, etc. of this configuration will be explained. Also, firstly as a standard setting, the electromagnetic wave 31 is detected by the first and second detection unit 121, 122 when the observation object 2 is not arranged, and a phase of the first detection signal or the second detection signal is advanced or retreated and adjusted by the signal processing part 125 so as to make a resulting phase of the first detection signal and that of the second detection signal equal. Then, when the observation object 2 is set, the reference electromagnetic wave 32 and the signal electromagnetic wave 33 are detected, and based on the resulting first and second detection signal, an amount of a phase deviation (the phase difference) of the second detection signal to the first detection signal is detected.

Also, in the above-mentioned observation device 1 shown in FIG. 1, the reference electromagnetic wave 32 and the signal electromagnetic wave 33 were individually detected by the first detection unit 121 and the second detection unit 122. As an alternative example associated with this point, the reference electromagnetic wave 32 and the signal electromagnetic wave 33 are overlapped by a waveguide means and the resulting interference wave may be detected by the first detection unit 121 and the second detection unit 122. And, information about a strength of the interference wave, etc. acquired as a result of the detection may be obtained by the signal processing part 125, and the result may be given to a control part 13. In this case, one of the detection unit 121 and the detection unit 122 may be omitted.

Also, while the above-mentioned observation device 1 shown in FIG. 1 has the configuration to move to the X, Y directions the second detection unit 122 that detects the signal electromagnetic wave 33, an alternative example associated with this point includes a following configuration. That is, the configuration has the second detection unit 122 provided with several detection components (e.g., a receiving antenna) that detect the signal electromagnetic wave 33 arranged in almost linear or planar way. Several arrangements forms of the detection component include, for example, a form to arrange the detection component in almost linear way along the X direction or the Y direction or a form to arrange the detection component in almost planar order (e.g., in a matrix state of several rows, and several columns) along a XY plane. In this case, a whole or a part of functions of the second, driving part 124 to move the second detection unit 122 to the X, Y directions may be omitted.

Then, the result of the actual observation of the observation object 2 using an optical coherent tomography 1A shown in FIG. 12 will be explained. The optical coherent tomography 1A shown in FIG. 12 is a specific example of the observation device 1 in FIG. 1 and by adding identical reference numbers to parts corresponding to the configuration in FIG. 1, duplication of explanation is avoided.

Figure 12:
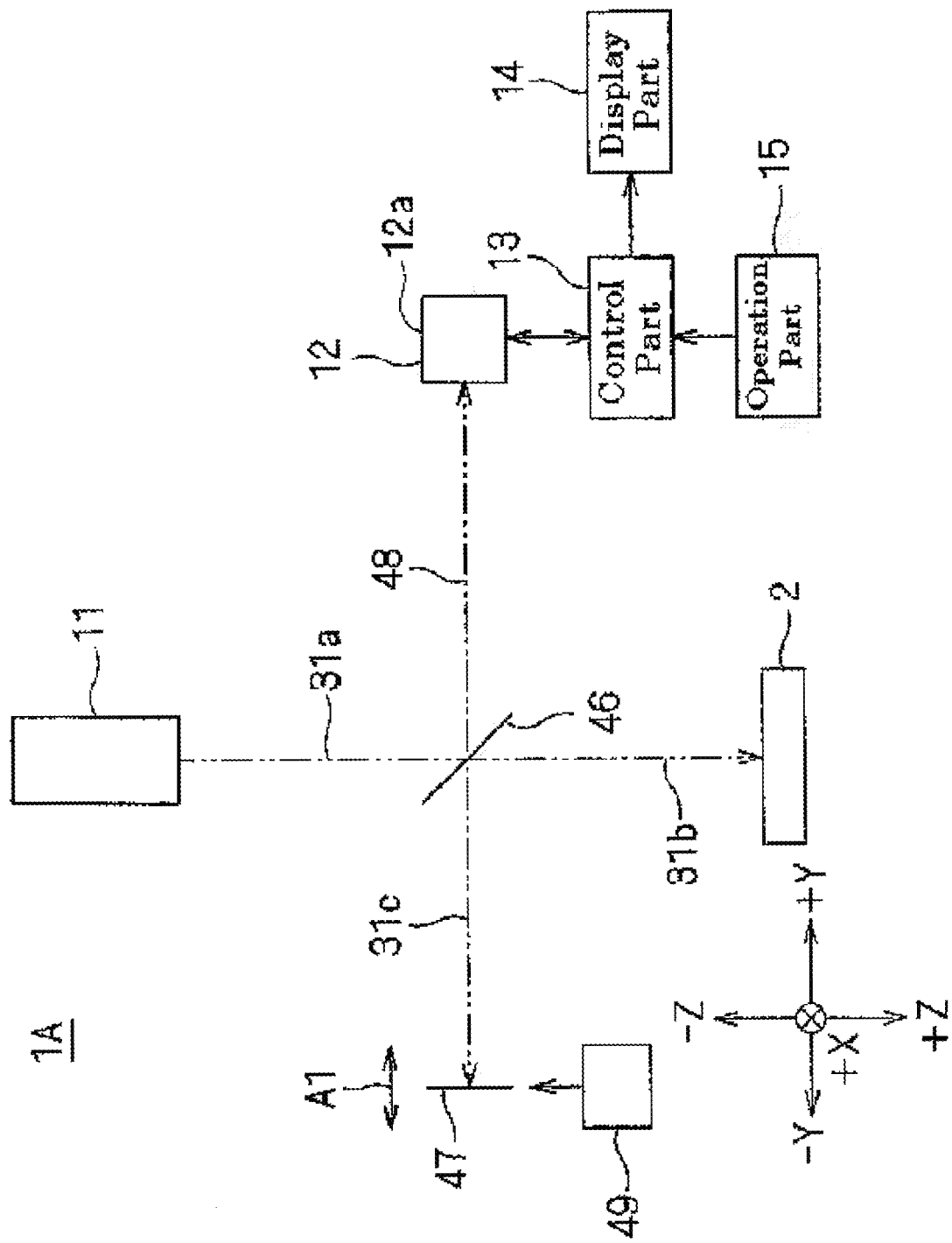
FIG. 12 It is a block diagram showing a configuration of an optical coherence tomography, which is a concrete example of the observation device in FIG. 1.

In this optical coherent tomography 1A, the output part 11 outputs the pulsed laser light 31a shown in FIG. 10 and FIG. 12 as an electromagnetic wave for observation. More specifically, the output part 11 is comprised of a mode locking titanium sapphire ultrashort pulsed laser device as a light source unit. A pulse frequency of the pulsed laser light 31a is 82 MHz, and an output level per second is about 15 mW.

Also, a divisional binding optical system 46 is equipped with this optical coherent tomography 1A. This divisional binding optical system 46 divides the pulsed laser light 31a outputted from the output part 11 into the irradiation light 31b toward the observation object 2 and the reference light 31c toward a reference object 47 (e.g., a mirror) and produces the interference light 48 by overlapping the reflected light of the irradiation light 31b reflected by the observation object 2 and the reflected light of the reference light 31c reflected by the reference object 47. As a major component of the divisional binding optical system 46, a half mirror is used in a configuration shown in FIG. 12, but a branched type of optical fiber (or a light guide plate) with two input/output terminals which branch into both entrance and exit sides of the light may be used.

An optical path length between the divisional binding optical system 46 and the observation object 2 and an optical path length between the divisional binding optical system 46 and the reference object 47 are set to be substantially equal, and when a light path length of the irradiation light 31b reaching to the divisional binding optical, system 46 after reflected, by the observation object 2 and a light path length of the reference light 31c reaching to the divisional binding optical system 46 after reflected by the reference object 47 are equal, a strength of the interference light 48 produced by the two reflected, waves forms the maximum value. On the other hand, as shown in the example of FIG. 4, in case of the observation object 2 with an internal structure, reflected lights of the irradiation lights 31 from the observation object 2 include several lights which differ in reflected positions in depth direction within the observation object 2.

Therefore, when the light path length of the reference light 31b is changed by driving (scanning) the reference object 47 as shown with the arrow A1 along a optical axis direction (an entrance direction) where the reference light 31b enters the reference object 47, every time a light path length of the reference light 31b corresponds to a light path length of each light which differs in reflected, positions towards the depth within the observation object 2 contained in the reflected light of the irradiation light 31b, a strength of the interference light 48 outputted by the divisional binding optical system 46 forms the maximum value. Thus, based on position information about the reference object 47 and information about the strength of the interference light 48, information about the cross-sectional structure of the observation object 2 (a tomographic image, etc.) can be obtained. The reference object 47 is movable along the direction shown with the arrow A1 (the optical axis direction of the reference light 31c) and driven towards a direction shown with the arrow A1 by the driving part 49 operated under control of the control part 13. As an alternative example, instead of driving the reference object 47 along the optical axis direction of the reference light 31c, the observation object 2 may be driven along the optical axis direction of the reference light 31c by the driving part 49.

Furthermore, when this optical coherent tomography 1A obtains a cross-sectional image along a predetermined direction of the observation object 2 (e.g., the Y axis direction in FIG. 12), it moves an entrance position of the irradiation light 31a into the observation object 2 to the Y axis direction and detects a cross-sectional structure of the observation object 2 in each coordinate point of the Y axis direction. The movement of the entrance position on the observation object 2 of the irradiation light 31a is done for example, by inserting an optical system for an optical path conversion which moves an optical path of the irradiation light 31a in the Y axis direction to the optical path of the irradiation light 31a, etc. or moving the observation object 2 in the Y axis direction with respect to a optical coherent tomography 2A.

Figure 13:
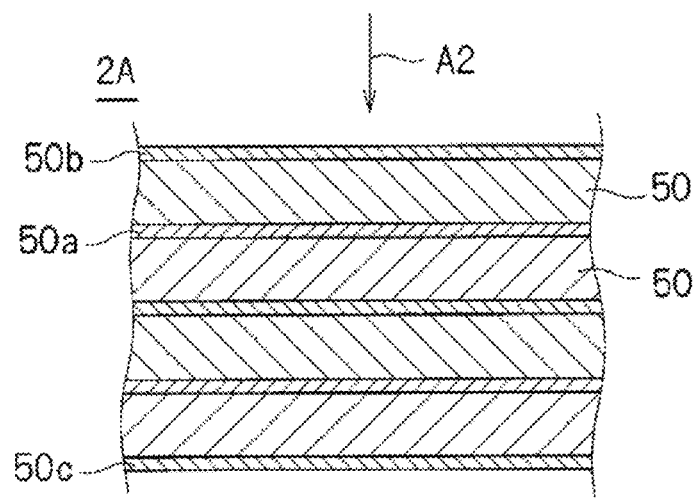
FIG. 13 It is a cross sectional view schematically showing a cross-sectional configuration of a mending tape laminate, which is a first test structure.

A light receiving unit 12a of the detection part 12 receives the interference light 48 outputted by the divisional binding optical system 46, converts it to an electrical signal (a detection signal), and sends it to the control part 13. For example, the light receiving unit 12a is comprised of a semiconductor light receiving element such as an avalanche diode. Also, an optical system such as a lens to adjust the interference light 48 entering the light receiving unit 12a may be arranged anterior to the light receiving unit 12a of the detection part 12. The control part 13 drives the reference object 47 to the direction shown with the arrow A1 via the driving part 49, and forms information about the cross-sectional structure of the observation object 2 (the tomographic image, etc.) by analyzing a process based on position information of the reference object 47 and information obtained by the detection signal (information about the strength of the interference light, etc.), FIG. 13 is a cross-sectional view schematically illustrating the cross-sectional structure of a first test structure 2A used as the observation object 2. This first test structure 2A is prepared by immersing into a solution a mending tape laminate consisting of sheets of 4 mending tapes 50 taped all together, i.e., a test material, only for a predetermined time. By immersing the mending tape laminate into the solution, the solution soaks into a narrow gap between each laminated mending tape 50 and forms a thin layer 50a of the solution between the mending tapes 50. At the same time, if there is an affinity with the solution or the medium dissolved in the solution and a tape substrate of the mending tape 50, the thin layer 50b consisting of the solution or the medium dissolved in the solution is also formed on a surface of the mending tape laminate. Also, if there is an affinity with the solution or the medium dissolved in the solution and an adhesive given on a back surface of the tape substrate of the mending tape 50, the thin layer 50c consisting of the solution or the medium dissolved in the solution is also formed on a back surface of the mending tape laminate. Additionally, a thickness of one layer of the mending tape used in the test structure 2A is about 40-50 μm and a thickness of the tape substrate is about 20-30 μm and the remaining thickness part consists of the part of the adhesive and the gap. The arrow A2 in FIG. 13 snows an entrance direction of the irradiation light 31b into the test structure 2A.

Now, four tapes of first test structure 2A are prepared by immersing the mending tape laminate into a brilliant blue solution; into a pentacene ethanol solution; into an ICG solution; and into water. However, when water is used as a test material, the mending tape laminate is removed from water, due to a low affinity with water and the tape substrate of the mending tape, and therefore water is repelled by the tape substrate and not left on the surface of the mending tape laminate, and the thin layer 50b is not formed. Also, when the brilliant blue solution is used as a test material, the mending tape laminate is removed from the brilliant blue solution, due to a low affinity with water and its solute, the brilliant blue and the tape substrate of the mending tape, and therefore the brilliant blue solution is repelled by the tape substrate and not left on the surface of the mending tape laminate, and the thin layer 50b is not formed. When the pentacene ethanol solution is used as a solution, due to a high affinity with the solute, pentacene and the tape substrate of the mending tape, the mending tape laminate is dipped into the solution (after the mending tape laminate is removed, solvent, i.e., ethanol vaporizes), to form a thin layer 50b consisting of the pentacene on the surface of the mending tape laminate. When the ICG solution is used as a solution, due to a high affinity with the solute, ICG and the tape substrate of the mending tape, the mending tape laminate is dipped into the solution (after the mending tape laminate is removed, solvent, i.e., water vaporizes), to form a thin layer 50b consisting of the ICG on the surface of the mending tape laminate. Since the back surface of the mending tape laminate has a high affinity with the adhesive, and water and each solute, a thin layer 50b of the brilliant blue, pentacene, or ICG is formed by immersing the mending tape laminate into each solution. Also, when the mending tape laminate is dipped into water, water adhered to the back surface of the mending tape laminate vaporizes, and thus a thin layer 50c of water on the back surface is observed, in the absence of water.

Figure 14:
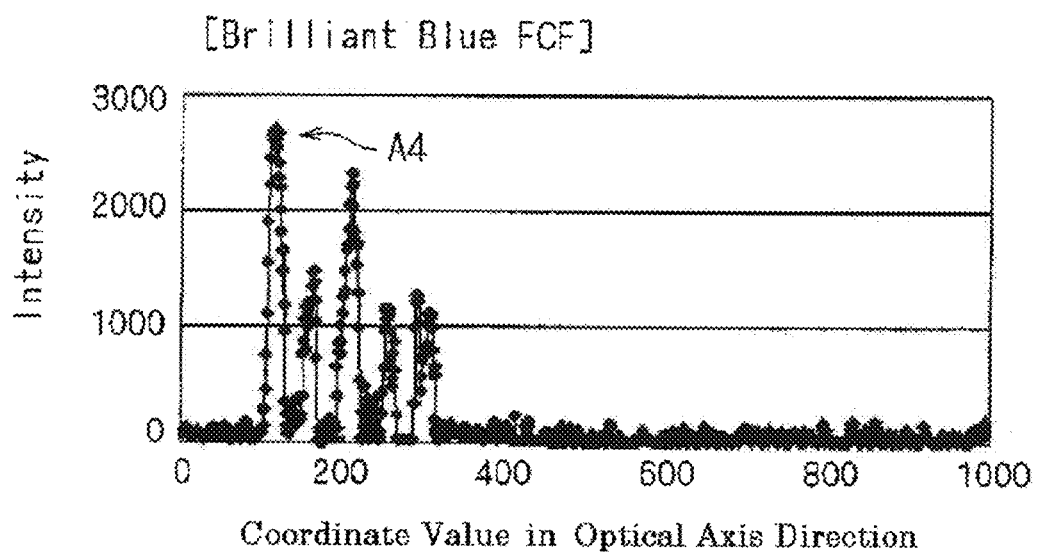
FIG. 14 It is a graph showing a detection, signal obtained, by observation using the mending tape laminate in FIG. 13 soaked in the brilliant blue solution.
Figure 15:
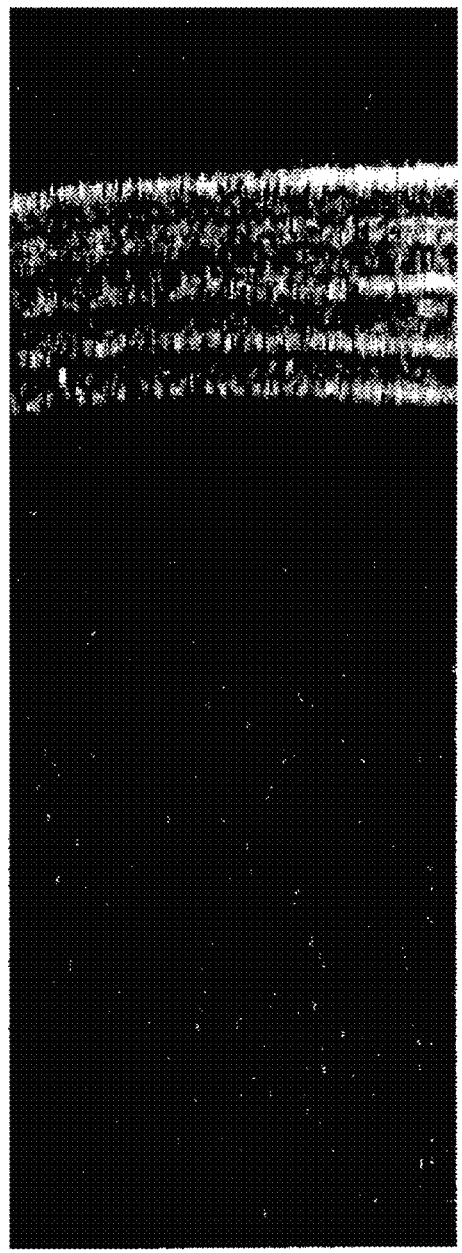
FIG. 15 It shows a tomographic image formed based on the detection signal obtained by the observation in FIG. 14, FIG. 16 It is a graph showing the detection signal obtained, by the observation using the mending tape laminate in FIG. 13 soaked in the pentacene ethanol solution.
Figure 16:
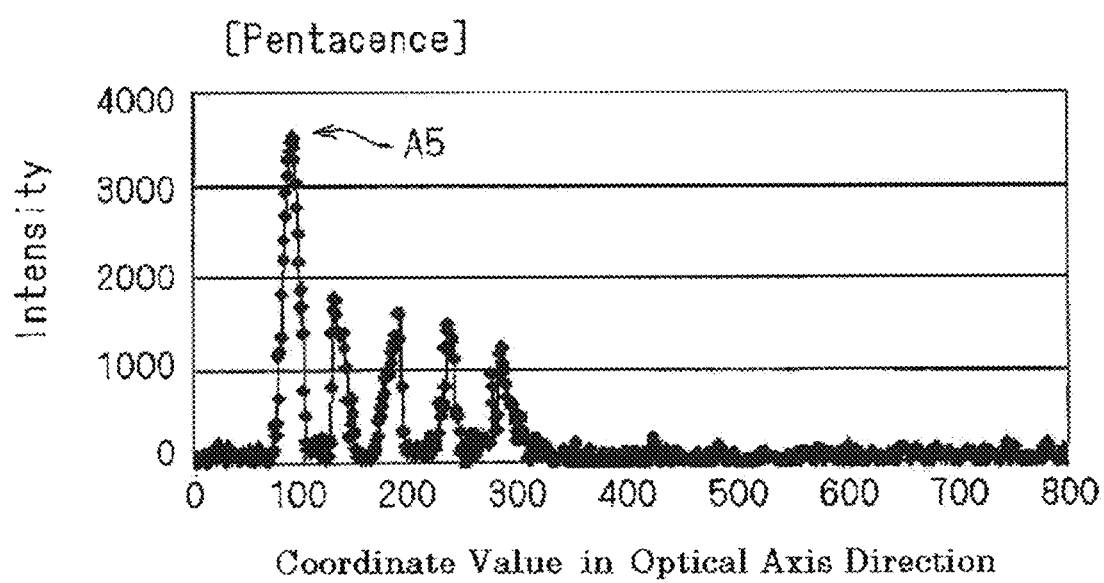
Figure 17:
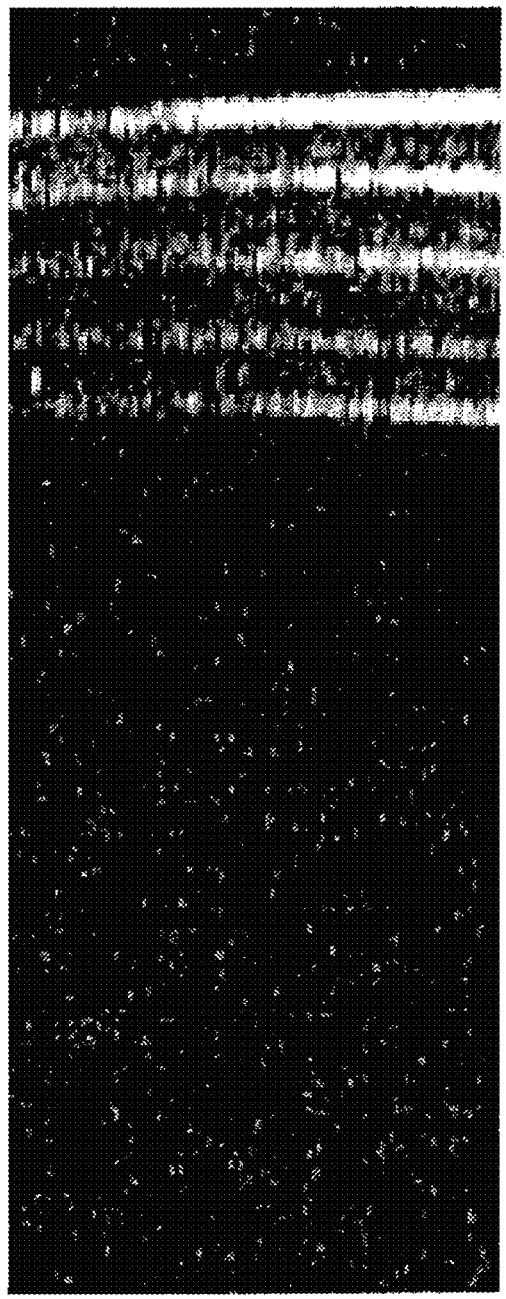
FIG. 17 It shows a tomographic image formed based on the detection signal obtained by the observation in FIG. 16, FIG. 18 It is a graph showing the detection signal obtained by the observation using the mending tape laminate in FIG. 13 soaked in the indocyanine blue solution.
Figure 18:
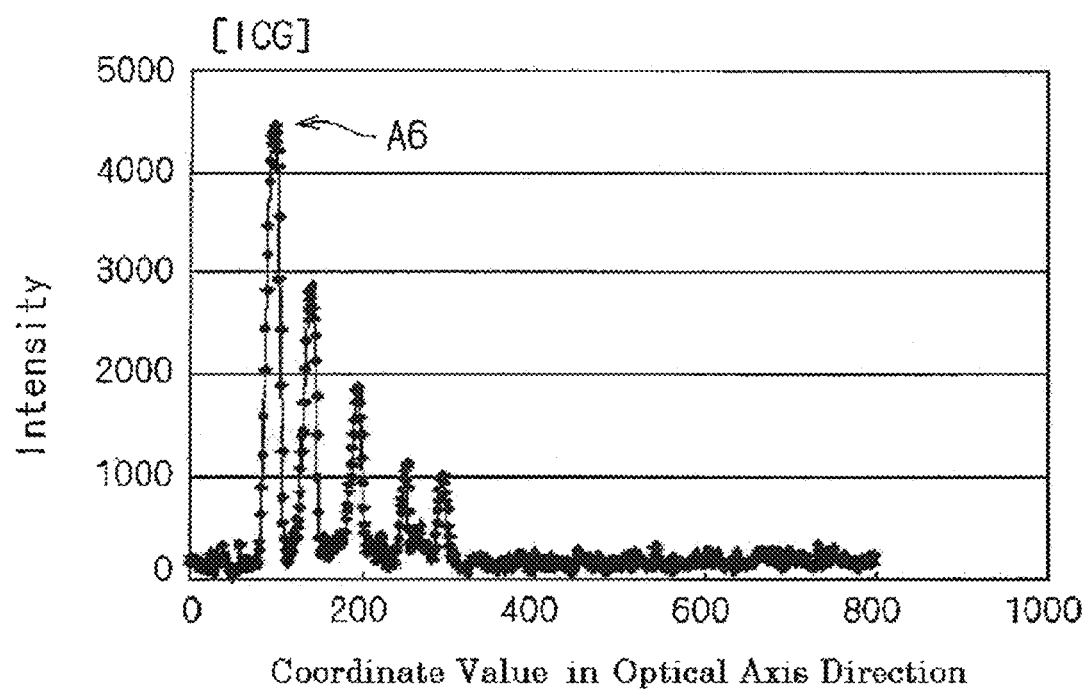
Figure 19:
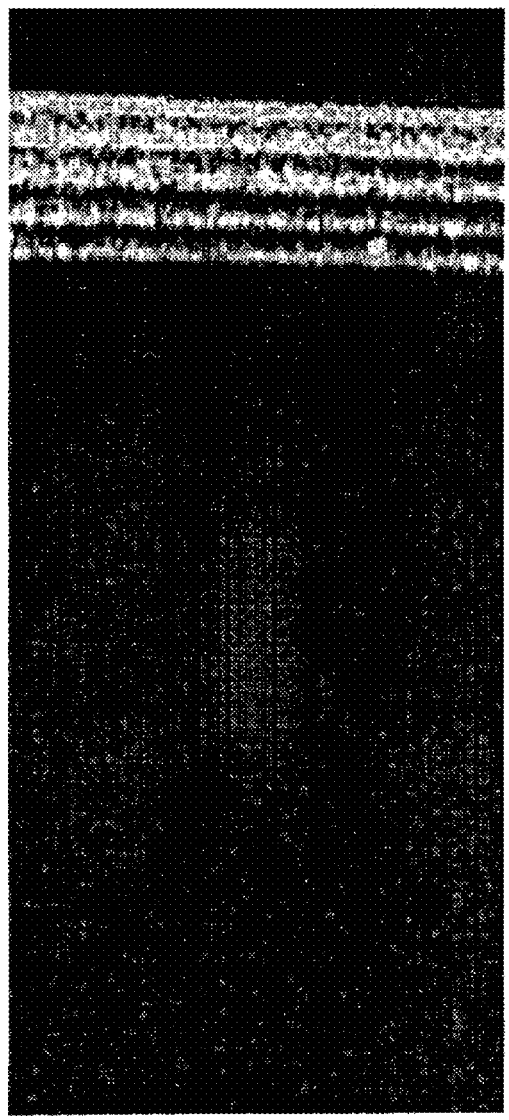
FIG. 19 It shows a tomographic image formed based on the detection signal obtained by the observation in FIG. 18.
Figure 20:
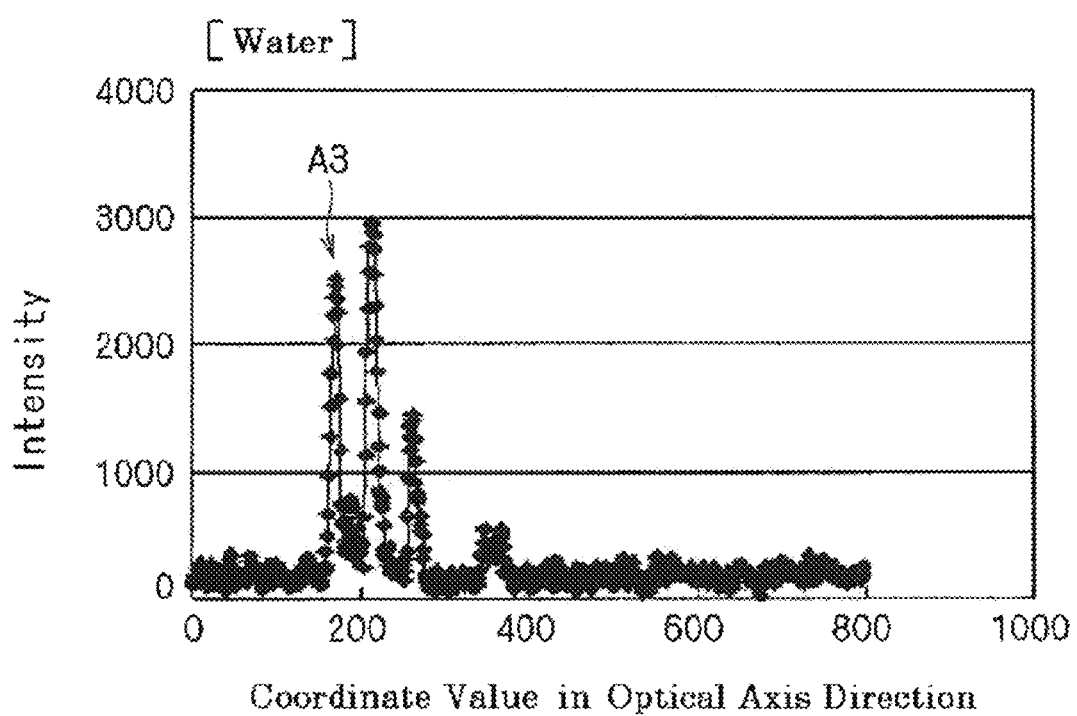
FIG. 20 It is a graph showing the detection signal obtained by the observation using the mending tape laminate in FIG. 13 soaked in the water.
Figure 21:
FIG. 21 It shows a tomographic image formed based on the detection signal obtained by the observation in FIG. 20.

The observation results are shown in FIG. 14 to FIG. 21. FIGS. 14 and 15 show the observation results when using the mending tape laminate immersed into the brilliant blue solution. FIGS. 16 and 17 show the observation results when using the mending tape laminate immersed into the pentacene ethanol solution. FIGS. 18 and 19 show the observation results when using the mending tape laminate immersed, into the ICG solution. FIGS. 20 and 21 show the observation results when using the mending tape laminate immersed into water. Also, horizontal axises in graphs of FIGS. 14, 16, 18, and 20 correspond to coordinate values of the reference object 47 along the optical axis direction, of the reference light 31c, and vertical axises represent numeral values of a strength of the interference light received by the light receiving unit. A peak of the waveform in a pulse form, among the signal waveforms shown in these graphs, corresponds to the surface (or the thin layer 50b of the solution formed, on the surface), the back surface (or the thin layer 50c formed on the back surface), and the thin layer 50a of the solution formed in a gap between each mending tape 50 of the mending tape laminate in the first test structure 2A.

Furthermore, in the observation here, an irradiation with the pulsed laser light 31a was conducted for 1.5 seconds for each coordinate value (coordinate point) of the reference object 47, while the reference light 31c of the reference object 47 was moved along the optical axis direction at a predetermined pitch. Thus, strength values of the interference lights in each coordinate value (coordinate point) in FIGS. 14, 16, 18, and 20 correspond to integrated values of a amount of received lights of the interference lights for 1.5 seconds.

FIGS. 15, 17, 19, and 21 show the tomographic image formed, based, on the detection results in FIGS. 14, 16, 18, and 20. White lines extending to a horizontal direction in FIGS. 15, 17, 19, and 20 correspond to a part in which a solution, i.e., a test sample between each mending tape in the mending tape laminates is soaked (a thin layer 50a of the solution), and a surface and a back surface of the mending tape laminates (or a thin layer 50b, 50c of the solution formed on the surface or the back surface).

Referring to FIGS. 20 and 21, the observation results using the mending tape laminate immersed into water will be explained. Now, according to the graph in FIG. 20, the surface of the mending tape laminate is detected, and a first and a second layer of the thin layer 50a, of three water thin layers 50a formed between the mending tape laminates, are detected, while a third layer of the thin layer 50a and the back surface of the mending tape laminate 50 are unclearly detected. Also, As for the cross-sectional image in FIG. 21, images of a third layer of the thin layer 50a and the back surface of the mending tape laminate 50 are not clear. Based on the results of the observation using water for this test material, the results of the observation using the brilliant blue solution, i.e., pentacene ethanol solution, or ICG solution for a test material are examined.

When the mending tape laminate immersed into the brilliant blue solution is used, the surface of the mending tape laminate is clearly detected according to the graph in FIG. 14. However, a thin layer 50b of three brilliant blue solutions formed, between the mending tape laminates and a thin layer 50c of the brilliant blue formed on the back surface of the mending tape laminate are unclearly detected. Thus, it turns out that there is little induction effect of the electromagnetic wave obtained with the brilliant blue solution. Even comparing the detection signal value of the surface of the mending tape laminate shown with the arrow A3 in FIG. 20 with the detection signal value of the surface of the mending tape laminate shown with the arrow A4 in FIG. 14, no effective differentials can be obtained. Also, as for the cross-sectional image in FIG. 15, Images of the surface of the mending tape laminate, each thin layer 50a between the mending tapes, and the thin layer 50c of the back surface are not clear.

When the mending tape laminate immersed into the pentacene ethanol solution is used, a thin layer 50b, 50c formed on the surface and the back surface of the mending tape laminate and each thin layer 50b between the mending tapes are clearly detected according to the graph in FIG. 16. Thus, it turns out that an induction effect of the electromagnetic wave obtained with the pentacene ethanol solution or pentacene is efficiently obtained. A sensitization (a value by dividing the detection signal value shown with the arrow A5 in FIG. 16 by the detection signal value shown with the arrow A3 in FIG. 20), compared to that obtained by immersing the mending-tape laminate into water, also increases by 1.33 times. From this aspect, it turns out that a valid sensitization effect is obtained. Also, As for the cross-sectional image in FIG. 17, clearness of the image of each thin layer 50a-50c wholly increases.

When, the mending tape laminate immersed into the ICG solution is used, 50c formed, on the surface and the back surface of the mending tape laminate and each thin layer 50b between the mending tapes are very clearly detected according to the graph in FIG. 18, a thin layer 50b. Thus, it turns out that a strong induction effect of the electromagnetic wave obtained with the ICG solution or ICG is obtained. Its sensitization (a value by dividing the detection signal value shown with the arrow A6 in FIG. 18 by the detection signal value shown with the arrow A3 in FIG. 20), compared to that obtained, by immersing the mending tape laminate into water, also increases by 1.78 times. From this aspect, it turns out that a high sensitization effect is obtained. Also, As for the cross-sectional image in FIG. 19, clearness of the image of each thin layer 50a~50c wholly increases.

Figure 22:
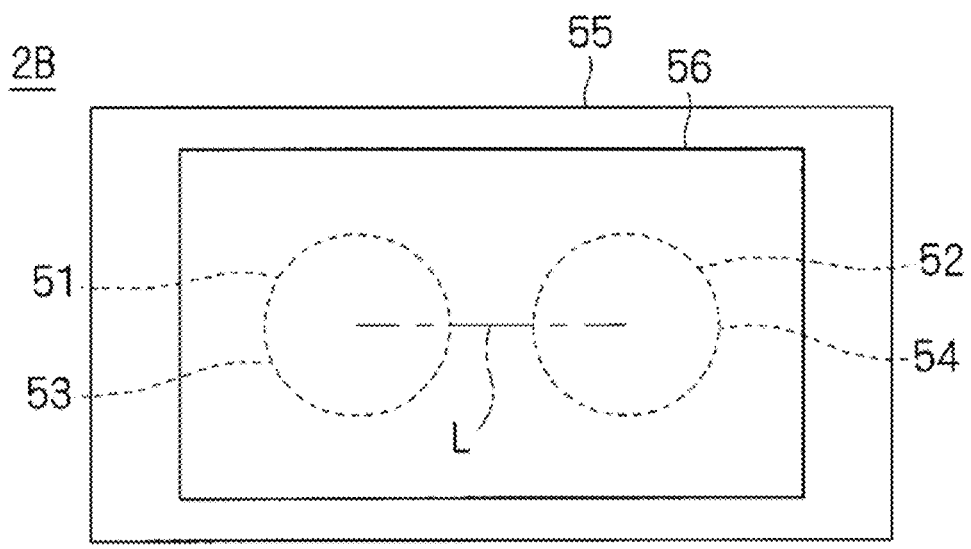
FIG. 22 It is a planar view showing a configuration of a second test structure having two, i.e. a first and a second cell parts.
Figure 23:
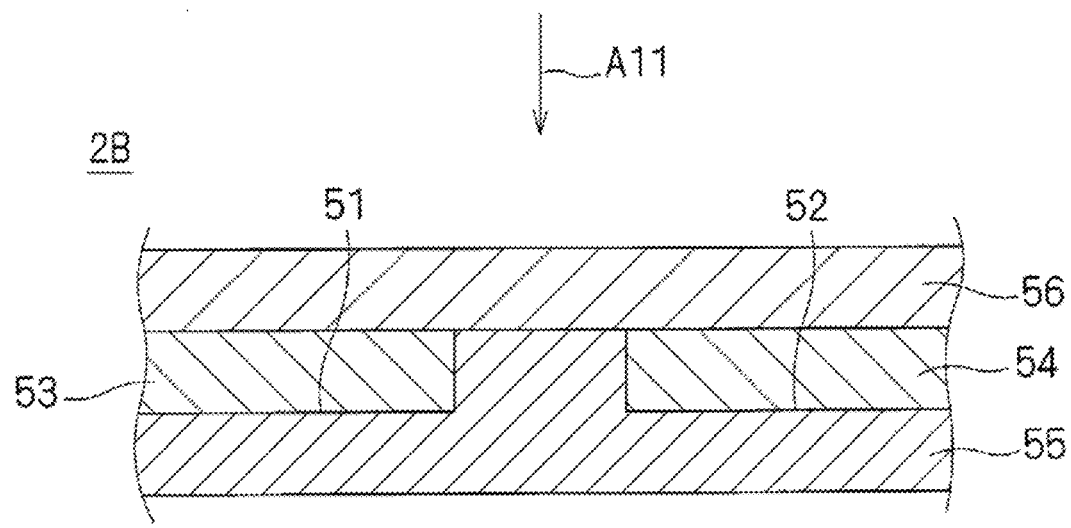
FIG. 23 It is a cross sectional view showing a cross sectional configuration along a cross sectional line L of the second test structure in FIG. 22.

Then, in order to intelligibly show the difference between the induction, effects of electromagnetic waves of water and the ICG solution, a following test was conducted using a light coherent tomography 2A in FIG. 12. As shown in FIGS. 22 and 23, the test is conducted using the second test structure 2B with which first and second cell parts 51, 52 are provided. Water 53 is stored in the first cell part 51 and the ICG solution 54 is stored, in the second cell part 52. Each cell part 51, 52 is formed by shaping two concave parts with a depth of 2 mm on the surface of an acrylic plate 55 and covering with a thin glass plate 56 a surface of the acrylic plate 55 with the concave parts. And, the second test structure 2B is irradiated with an irradiation light 31b from the light coherent tomography 2A from the direction shown with the arrow A11 in FIG. 23.

Figure 24:
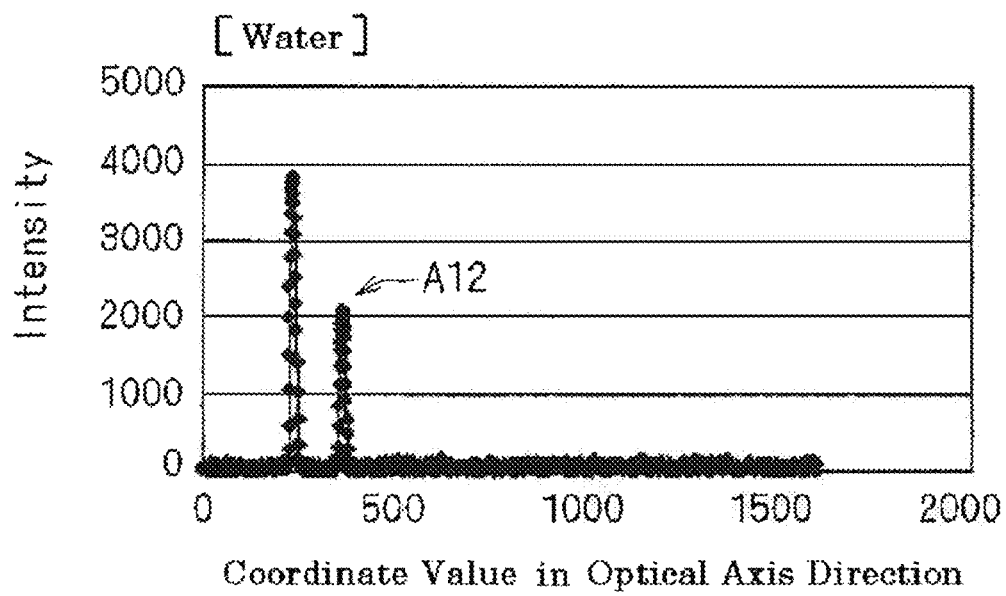
FIG. 24 It is a graph, showing a detection signal obtained by observation of the first cell part in FIG. 22 filled with water.
Figure 25:
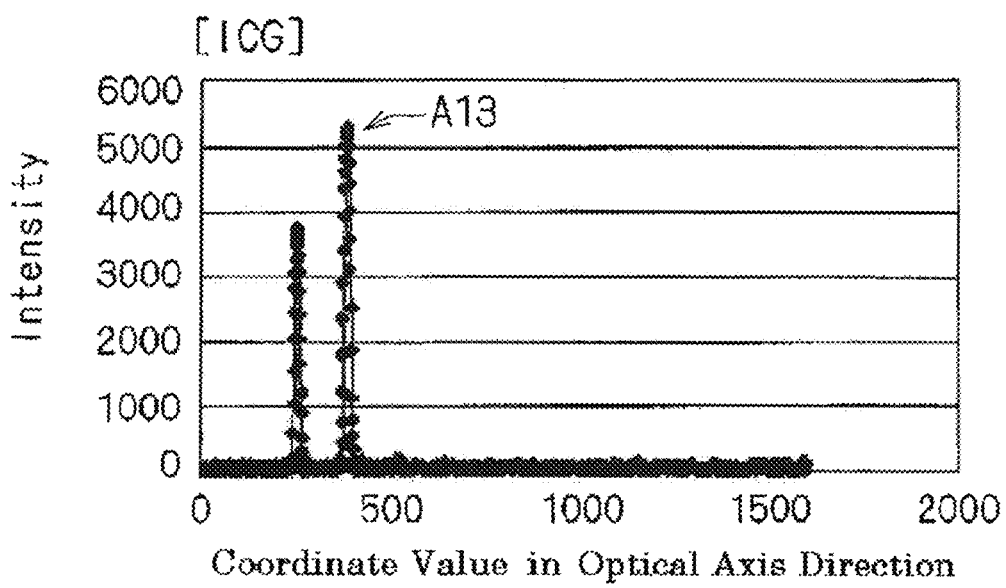
FIG. 25 It is a graph showing a detection signal obtained by observation of the second, cell part in FIG. 22 filled with, the indocyanine blue solution.

FIG. 24 shows a graph of a detection signal obtained, when, the first cell, part 51 storing water 53 is observed. FIG. 25 shows a graph of a detection signal obtained when the second cell part 52 storing the ICG solution 54 is observed. Configurations of horizontal axises and vertical axises of the graphs in FIGS. 24 and 25 are same as those of the graph in the above-mentioned FIG. 14, etc. In the graphs of FIGS. 24 and 25, a first peak of the signal waveform shows that a reflection on the surface of the glass plate 56 of the second test construction 2B was detected. Peaks shown with the arrow A12, 13 are worth noting, and these peaks correspond to a reflection on a boundary surface between the glass plate 56 and water 52 or the ICG solution 54.

According to the observation results in FIGS. 24 and 25, it turns out that a reflection strength of an irradiation light 31b on the boundary surface between the glass plate 56 and the ICG solution 54, as compared to water 52, is greatly improved, and thus a valid induction effect of the electromagnetic wave is obtained.

Figure 26:
FIG. 26 It shows a cross sectional image related to a cross sectional configuration along a cross sectional line L of the second test structure in FIG. 22 formed based on the detection signal.

FIG. 26 shows an image of the cross-sectional configuration along the cross-sectional line L of the second test structure in FIG. 22, formed based on the detection signal in FIGS. 24 and 25. A white line extending to a horizontal direction shown with the arrow A14 in the left side area in FIG. 26 corresponds to a boundary surface between water 53 and the glass plate 56, and a white line extending to a horizontal direction shown with the arrow A15 in the right side area in FIG. 26 corresponds to the boundary surface between the ICG solution 54 and the glass plate 56. Also in a cross-sectional image in FIG. 26, it turns out that the white line with the arrow A15 is remarkably clearer than with the arrow A14.

DESCRIPTION OF THE REFERENCE NUMERALS 1 observation device
1A light coherent tomography
2 observation object
2A first test structure
2B second test structure
11 output part
12 detection part
13 control part
14 display part
15 operation part
21, 22 medium
31 electromagnetic wave
31a pulsed laser light
31b irradiation light
31c reference light
32 reference electromagnetic wave
33 signal electromagnetic wave
46 divisional binding optical system
47 reference object
48 interference light
49 driving part
121 first detection unit
122 second detection unit
123 first driving part
124 second driving part
125 signal processing part.

The invention claimed is:
1. An observation device for observing an observation object, including an induction factor whose dipole moment changes by induction with an electromagnetic wave, the device comprising:
an output part which outputs an electromagnetic wave and changes the dipole moment of said induction factor included in said observation object by the outputted electromagnetic wave;
a detection part which detects a signal electromagnetic wave coming through said observation object and a reference electromagnetic wave coming without passing through said observation object among electromagnetic waves outputted by said output part; and
an analysis part which analyzes structures of said observation object based on detection result by said detection part; and
wherein said electromagnetic wave outputted by said output part is a pulsed laser light which is continuously outputted in pulses;
wherein wavelength of said electromagnetic wave outputted by said output part is set to be within an absorption wavelength region of said induction factor causing absorption by said induction factor of irradiated electromagnetic wave; and wherein wavelength of said electromagnetic wave outputted by said output part is set to a value so that absorbance of the electromagnetic wave by said induction factor is beyond a certain lower limit reference level and below a certain upper limit reference level when said induction factor is irradiated with the electromagnetic wave.

2. The observation device according to claim 1, wherein said pulsed laser light outputted as said electromagnetic wave by said output part is a femtosecond pulsed laser light.

3. The observation device according to claim 1, wherein pulse time width of said pulsed laser light outputted as said electromagnetic wave by said output part is shorter than duration from an entry of said pulsed laser light into said observation object to an emission of said electromagnetic wave in connection with a state transition of said induction factor within said observation object excited by said pulsed laser light.

4. The observation device according to claim 1, wherein the pulse time width of said pulsed laser light outputted as said electromagnetic wave by said output part is a value of 10 or more femtoseconds and 1 or less picoseconds.

5. The observation device according to claim 1, wherein said electromagnetic wave outputted by said output part is a laser light within a visible to near-infrared wavelength range.

6. The observation device according to claim 5, wherein said observation object is a biological tissue.

7. The observation device according to claim 5, wherein said observation object is a biological tissue and wherein said induction factor is Indocyanine Green.

8. The observation device according to claim 1, wherein said induction factor is a dye.

9. The observation device according to claim 8, wherein said induction factor is an organic dye.

10. The observation device according to claim 1, wherein said detection part detects an interference wave obtained by overlapping said reference signal electromagnetic wave and said signal electromagnetic wave.

11. The observation device according to claim 10, further comprising a divisional binding optical system to divide said pulsed laser light outputted by said output part into the irradiation light toward said observation object and the reference light toward a reference object and to produce an interference light by overlapping said irradiation light passing through said observation object and said reference light passing through said reference object, wherein said detection part detects said interference light obtained from said divisional binding optical system.

12. The observation device according to claim 1, wherein said detection part detects extent of change in said signal electromagnetic wave with reference to said reference signal electromagnetic wave.

13. A method of observing an observation object, comprising steps of:

introducing into said observation object an induction factor whose dipole moment changes by induction with an electromagnetic wave; and observing the observation object including outputting the electromagnetic waves from an outputting part, the irradiated waves changing the dipole moment of said induction factor within said observation object, detecting a signal electromagnetic wave coming through said observation object and a reference electromagnetic wave coming without passing through said observation object among electromagnetic waves outputted by said output part, and analyzing structure of said observation object based on detection result by said detection part, and wherein said electromagnetic wave outputted by said output part is a pulsed laser light which is continuously outputted by in pulses, wherein wavelength of said electromagnetic wave outputted by said output part is set to be within an absorption wavelength region of said induction factor causing absorption by said induction factor of the irradiated electromagnetic wave, and wherein wavelength of said electromagnetic wave outputted by said output part is set to a value so that absorbance of the electromagnetic wave by said induction factor is beyond a certain lower limit reference level and below a certain upper limit reference level when said induction factor is irradiated with the electromagnetic wave.

14. The method according to claim 13, said step of introducing an induction factor comprises a step of introducing into said observation object said induction factor in solution state when dissolved in a solvent.

15. The method according to claim 14, said step of introducing an induction factor comprises a step of introducing the solution of said induction factor into said observation object using an injection apparatus.

16. The method according to claim 14, said step of introducing an induction factor comprises a step of introducing the solution of said induction factor into said observation object by immersion, through surface of said observation object or through a gap between several mediums appeared on said surface of said observation object.

* * * * *